United States Patent
Oda et al.

(10) Patent No.: US 9,189,677 B2
(45) Date of Patent: *Nov. 17, 2015

(54) RECORDING MEDIUM HAVING OBSERVATION PROGRAM RECORDED THEREIN AND OBSERVATION APPARATUS

(71) Applicant: Panasonic Healthcare Holdings Co., Ltd., Minato-ku, Tokyo (JP)

(72) Inventors: Atsushi Oda, Osaka (JP); Mikio Houjou, Higashiosaka (JP)

(73) Assignee: PANASONIC HEALTHCARE HOLDINGS CO., LTD. (JP)

( * ) Notice: Subject to any disclaimer, the term of this patent is extended or adjusted under 35 U.S.C. 154(b) by 357 days.

This patent is subject to a terminal disclaimer.

(21) Appl. No.: 13/729,264

(22) Filed: Dec. 28, 2012

(65) Prior Publication Data

US 2013/0188033 A1    Jul. 25, 2013

Related U.S. Application Data

(63) Continuation of application No. PCT/JP2011/079763, filed on Dec. 22, 2011.

(30) Foreign Application Priority Data

Feb. 28, 2011 (JP) .................................. 2011-042418

(51) Int. Cl.
*H04N 9/47* (2006.01)
*G06K 9/00* (2006.01)
(Continued)

(52) U.S. Cl.
CPC ........ *G06K 9/00134* (2013.01); *G01N 15/1463* (2013.01); *G02B 21/0088* (2013.01); *G02B 21/365* (2013.01); *G01N 2015/1493* (2013.01); *G02B 21/0056* (2013.01)

(58) Field of Classification Search
USPC ........ 348/79, 46; 382/128, 133; 250/288, 282
See application file for complete search history.

(56) References Cited

U.S. PATENT DOCUMENTS 6,330,349 B1 * 12/2001 Hays et al. .................... 382/128
7,050,620 B2 *  5/2006 Heckman ...................... 382/133

(Continued)

FOREIGN PATENT DOCUMENTS

| JP | 2006-23644 A | 1/2006 |
| JP | 2006-91506 A | 4/2006 |

(Continued)

OTHER PUBLICATIONS

International Search Report for International application No. PCT/JP2011/079763 mailing date of Apr. 3, 2012 with English translation.

*Primary Examiner* — Gims Philippe
(74) *Attorney, Agent, or Firm* — Cantor Colburn LLP

(57) ABSTRACT

A recording medium having an observation program recorded therein, the program may cause a computer to execute: an entire-image-pickup process of picking up an image of a sample by picking up an image of an entire container containing the sample and a solution; a sample-mass-identification process of identifying a sample mass having the samples gathering therein, from the image picked up in the entire image-pickup process; a sample-mass-determination process of extracting shape information of the identified sample mass, and determining a state of the sample mass based on the shape information; a coordinate-detection process of selecting a magnifying-observation-target sample mass from the identified sample masses, and detecting coordinates of the center of the magnifying-observation-target sample mass.

14 Claims, 17 Drawing Sheets

(51) Int. Cl.
*G01N 15/14* (2006.01)
*G02B 21/00* (2006.01)
*G02B 21/36* (2006.01)

(56) References Cited

U.S. PATENT DOCUMENTS

| | | |
|---|---|---|
| 7,064,318 B2 * | 6/2006 | Bui .............................. 250/282 |
| 2010/0044563 A1 * | 2/2010 | Harada et al. ................ 250/288 |
| 2010/0128961 A1 | 5/2010 | Kalusche |
| 2011/0261164 A1 * | 10/2011 | Olesen et al. ................... 348/46 |

FOREIGN PATENT DOCUMENTS

| | | |
|---|---|---|
| JP | 2006-171183 A | 6/2006 |
| JP | 2008-212017 A | 9/2008 |
| JP | 2010-527007 A | 8/2010 |
| WO | 2008137912 A1 | 11/2008 |

* cited by examiner

RECORDING MEDIUM HAVING OBSERVATION PROGRAM RECORDED THEREIN AND OBSERVATION APPARATUS

CROSS-REFERENCE TO RELATED APPLICATIONS

This application is a continuation under 35 U.S.C. §120 of PCT/JP2011/079763, filed Dec. 22, 2011, which is incorporated herein reference and which claimed priority to Japanese Application No. 2011-042418, filed Feb. 28, 2011. The present application likewise claims priority under 35 U.S.C. §119 to Japanese Application No. 2011-042418, filed Feb. 28, 2011, the entire content of which is also incorporated herein by reference.

BACKGROUND

Description of the Related Art

In culturing cells, if observation can be started concurrently with emergence of a cell mass having a plurality of cells gathering therein and the observation can be conducted sequentially in chronological order, it can be a promising technique to support regenerative medicine, for example. Conventionally, such observation of cells has been conducted, by using a microscope, etc., when replenishment or replacement of culture fluid in a culture container is required during cell culture, and an image has been picked up as necessary.

However, observation of cells using a microscope requires much expense in time and effort. For example, in order to identify a cell mass having emerged in a container, first, the entire container needs to be observed visually or by using a microscope, and then, a growing state of the individual cell mass needs to be observed under magnification by replacing an objective lens. In magnifying observation, a narrow field of view causes difficulty in searching a target cell mass, and also difficulty in matching the cell mass with the field of view. When observing cells, it is preferable to conduct time-lapse observation in which a long-term change is observed from a time of emergence of the cell mass to a time of completion of growth thereof in every predetermined time period. Since the cell mass cannot be observed visually or by using a low-magnification microscope immediately after seeding of the cell, an observation position needs to be searched and set again several days later.

Further, in conventional observation that is conducted at the time of replenishment or replacement of culture fluid in a culture container usually once in one to three days, it is difficult to conduct observation from a time of emergence of a cell mass, and thus a technique capable of observation of a cell mass from the time of emergence thereof is in high demand. Further, in picking up an image of a cell in each of the cases where the entire container is observed and where a part of the interior of the container is observed under magnification, such a problem arises that heat generated from illumination, a lens driving system has effects on growth of the cell.

With respect to such observation of cells, a device has been proposed that is configured to save time and effort in switching between the observation of the entire container and the magnifying observation of a part of the interior of the container, and an example can be found in Japanese Laid-Open Patent Publication No. 2009-198709. The observation apparatus described in Japanese Laid-Open Patent Publication No. 2009-198709 includes at least two image-pickup optical systems having different magnifications for picking up images of an object to be observed, and a reference value of a low-magnification image is calculated such that the image feature of an image picked up by a high-magnification image-pickup optical system becomes substantially equal to the image feature of an image concurrently picked up in a low-magnification image-pickup optical system.

However, since the high-magnification image-pickup optical system and the low-magnification image-pickup optical system pick up images by using a common light source in the observation apparatus described in Japanese Laid-Open Patent Publication No. 2009-198709, a cell in the container cannot be observed in detail. That is because the high-magnification image-pickup optical system and the low-magnification image-pickup optical system require different types of illumination, respectively, that is, the high-magnification image-pickup optical system needs illumination such as a point source and a ring slit used in a phase-difference optical system suitable for observation of a substantially transparent cell in a micro region, while the low-magnification image-pickup optical system needs illumination such as planar light source suitable for observation of a relatively wide field of view. In other words, although distribution of cells in the container can be observed, it is concerned that identification of a cell mass having emerged in the container might fail or a target cell mass might be erroneously identified. Further, continuous observation from a time of emergence of a cell mass to a time of completion of growth thereof is not considered, either.

At least some present embodiments were made in view of the above points to provide an observation apparatus capable of identification of a sample mass having emerged through observation of the entire container and detailed observation of the identified sample mass by magnification thereof, in observing the sample such as a cell in the container. Further, at least some embodiments may provide an observation program and an observation system capable of continuous observation of such identified sample mass from a time of emergence thereof to a time of completion of growth thereof.

SUMMARY

A recording medium having an observation program recorded therein according to an aspect of the present invention, the observation program configured to cause a computer to execute: an entire image-pickup process of picking up an image of a sample by picking up an image of an entire container containing the sample and a solution; a sample mass identification process of identifying a sample mass having a plurality of the samples gathering therein, from the image picked up in the entire image-pickup process; a sample mass determination process of extracting shape information of the sample mass identified in the sample mass identification process, and determining a state of the sample mass based on the shape information; a coordinate detection process of selecting a magnifying observation target sample mass from the sample masses identified in the sample mass identification process, and detecting coordinates of a center of the magnifying observation target sample mass, based on a determination result of the sample mass determination process; and a magnifying image-pickup process of performing magnification with the coordinates detected in the coordinate detection process as a center of the magnification, and picking up an image of the magnifying observation target sample mass.

Other features will become apparent from descriptions of this specification and of the accompanying drawings.

BRIEF DESCRIPTION OF THE DRAWINGS

For more thorough understanding, the following description should be read in conjunction with the accompanying drawings, in which.

DETAILED DESCRIPTION OF THE INVENTION

Figure 1:
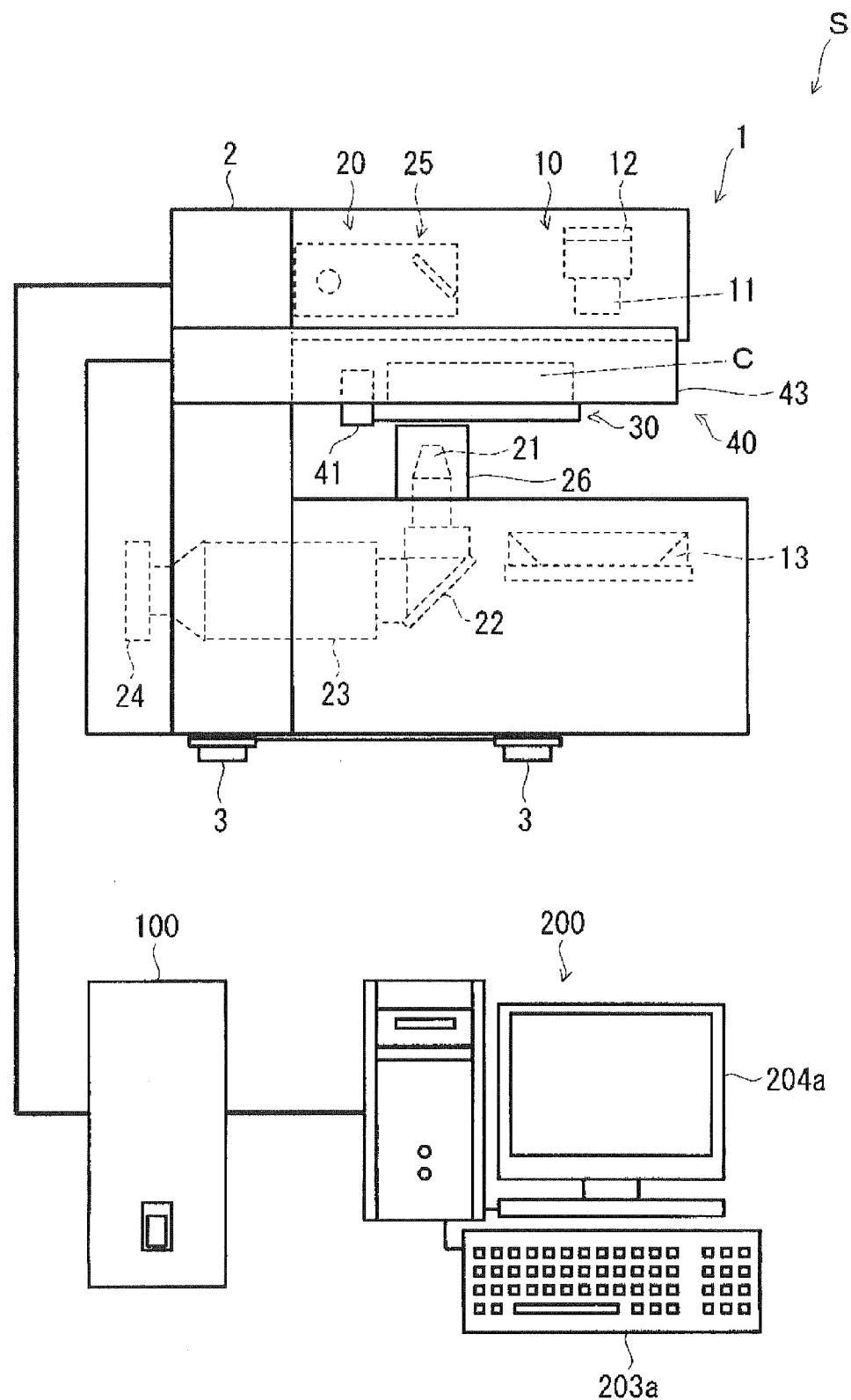
FIG. 1 is a configuration diagram of an observation system according to a first embodiment.

At least the following details will become apparent from descriptions of this specification and of the accompanying drawings.

In the following description, a "predetermined size" indicates a size of a sample mass set in advance and of the order of such a size that can be determined to be observed under magnification, and may be defined by the number of pixels on an image, for example. For example, if an image of a field of view with 40 mm×40 mm is picked up by a camera having 5 million pixels in entire observation, approximately 1000 pixels are appropriate as predetermined size. In embodiments of the present invention which will be described later, the "predetermined size" is set at "1000 pixels" for the number of pixels, but it is not limited thereto. The same also applies to the "predetermined size" used in the following means.

A "predetermined identification time period" (predetermined time period relating to identification of a sample mass) indicates a time period set in advance relating to timing for making identification of a sample mass to be observed under magnification target. It indicates a time period of the order of such a time period in which a time of emergence of the sample mass can be determined, and the time period can be set at from several hours to several days, for example, but can be appropriately set as necessary. Therefore, in embodiments of the present invention which will be described below, the "predetermined time period relating to identification of a sample mass" is set at "1 day" but it is not limited thereto. The wording "predetermined time period" used in other means does not necessarily indicate a time period relating to timing for making identification of the sample mass to be observed under magnification or does not indicate the same period in terms of time.

"The predetermined number of days for identification" (the predetermined number of days) is the number of days set in advance relating to timing for ending identification of the sample mass to be observed under magnification, and may be set at the arbitrary number of days such as 5, 7 or 10 days. In embodiments of the present invention which will be described later, "the predetermined number of days" is set at "5 days" but it is not limited thereto.

A "predetermined image-pickup period" (predetermined time period relating to image pickup of a magnified image) indicates a time period set in advance relating to timing for picking up an image of a magnified sample mass and of the order of such a period during which a growing process of the sample mass can be grasped. It can be set at a time period of from several hours to several days, for example, but can be set as appropriate as necessary. Therefore, in embodiments of the present invention which will be described below, the "predetermined time period relating to image pickup of a magnified image" is set at "1 day" but it is not limited thereto. The wording "predetermined time period" used in other means does not necessarily indicate a time period relating to timing for picking up an image of the magnified sample mass or does not necessarily represent the same time period in terms of time.

A "predetermined observation deadline" (predetermined deadline) is a deadline set in advance relating to timing for ending observation of a sample and may be set at an arbitrary deadline such as 10 days, 20 days or 30 days from the start of observation of the sample, for example. In embodiments of the present invention which will be described below, the "predetermined deadline" is set at "10 days", but it is not limited thereto.

A "predetermined shape" is a shape set in advance for a sample mass, and is preferably of the order of such a shape that can be determined to have a high possibility of continuously growing in such a manner as to be suitable for observation, is a circular shape to the highest degree possible, and can be set at an arbitrary numerical value such as an ellipse degree, for example. In embodiments of the present invention which will be described below, the "predetermined shape" is set at "an ellipse degree equal to or smaller than 1.1", but it is not limited thereto.

Hereinafter, embodiments of the present invention will be described on the basis of FIGS. 1 to 21. Here, a cell in samples such as a cell, a germ, a microorganism is described as a sample, and a culture fluid is described as a solution, for example. Further, a cell mass having a plurality of cells gathering therein is described as a sample mass.

<First Embodiment>

Figure 2:
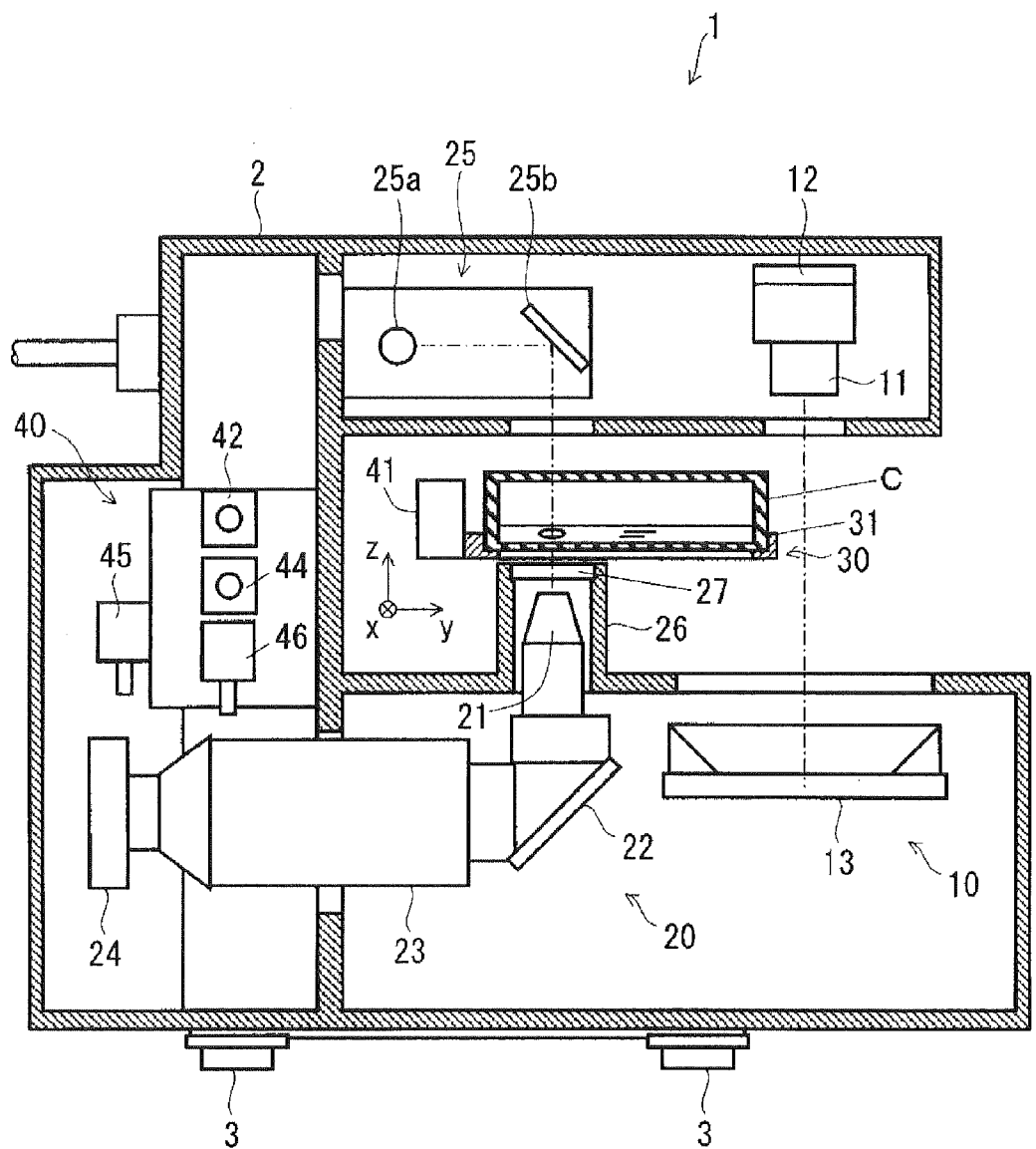
FIG. 2 is a perpendicular sectional side view of an observation apparatus of an observation system illustrated in FIG. 1.
Figure 3:
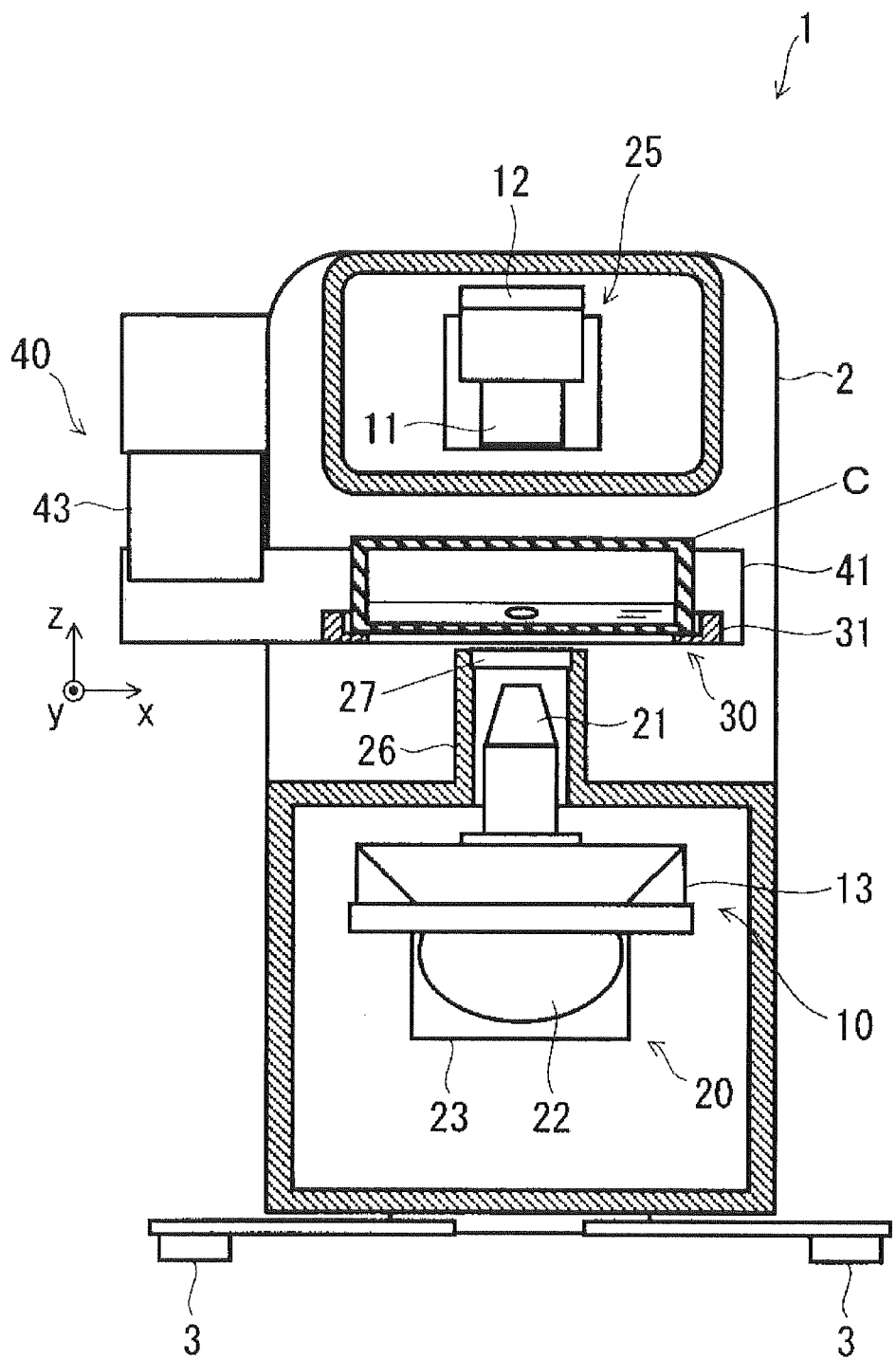
FIG. 3 is a perpendicular sectional front view of an observation apparatus of an observation system illustrated in FIG. 1.
Figure 4:
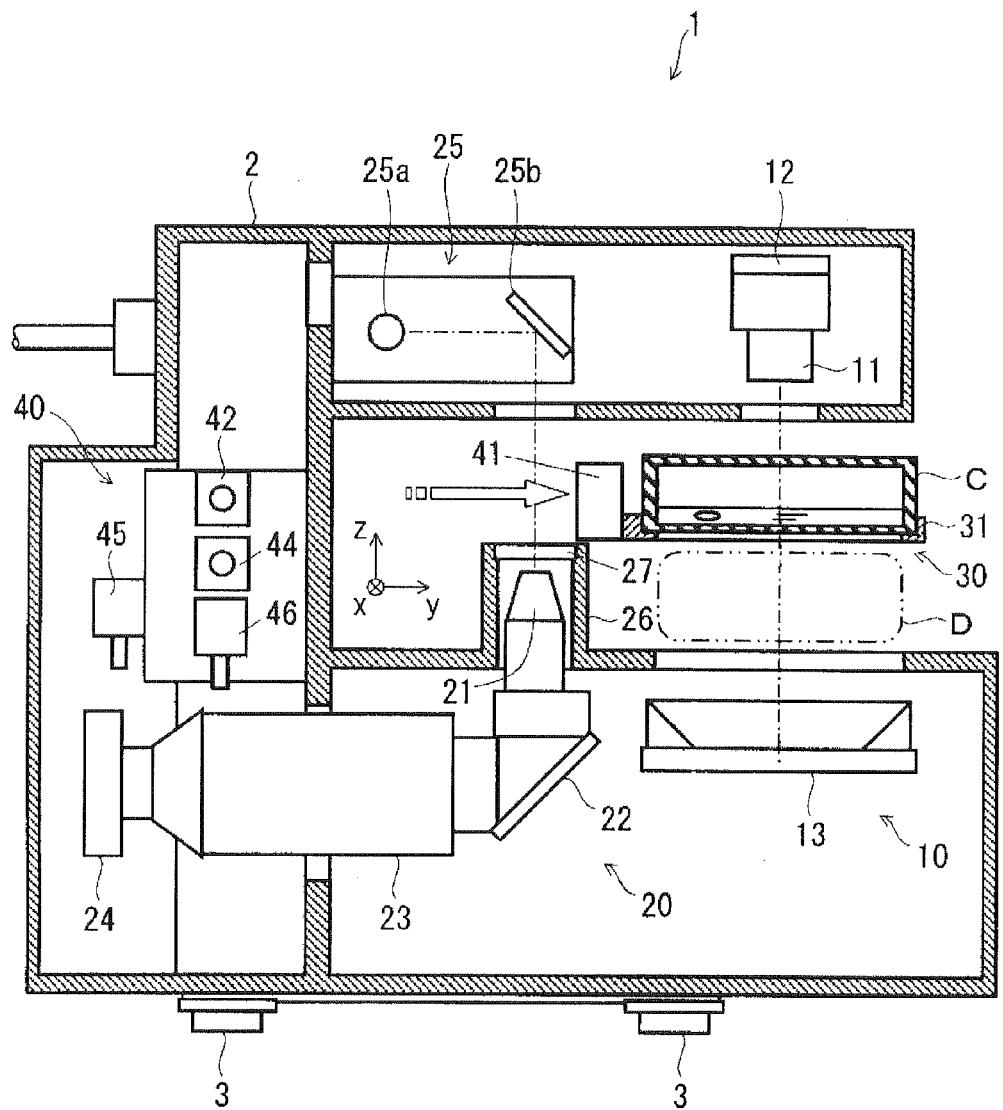
FIG. 4 is a perpendicular sectional side view of an observation apparatus similar to FIG. 2 and illustrates a state where a container has been moved to a spot corresponding to an entire observation unit.
Figure 5:
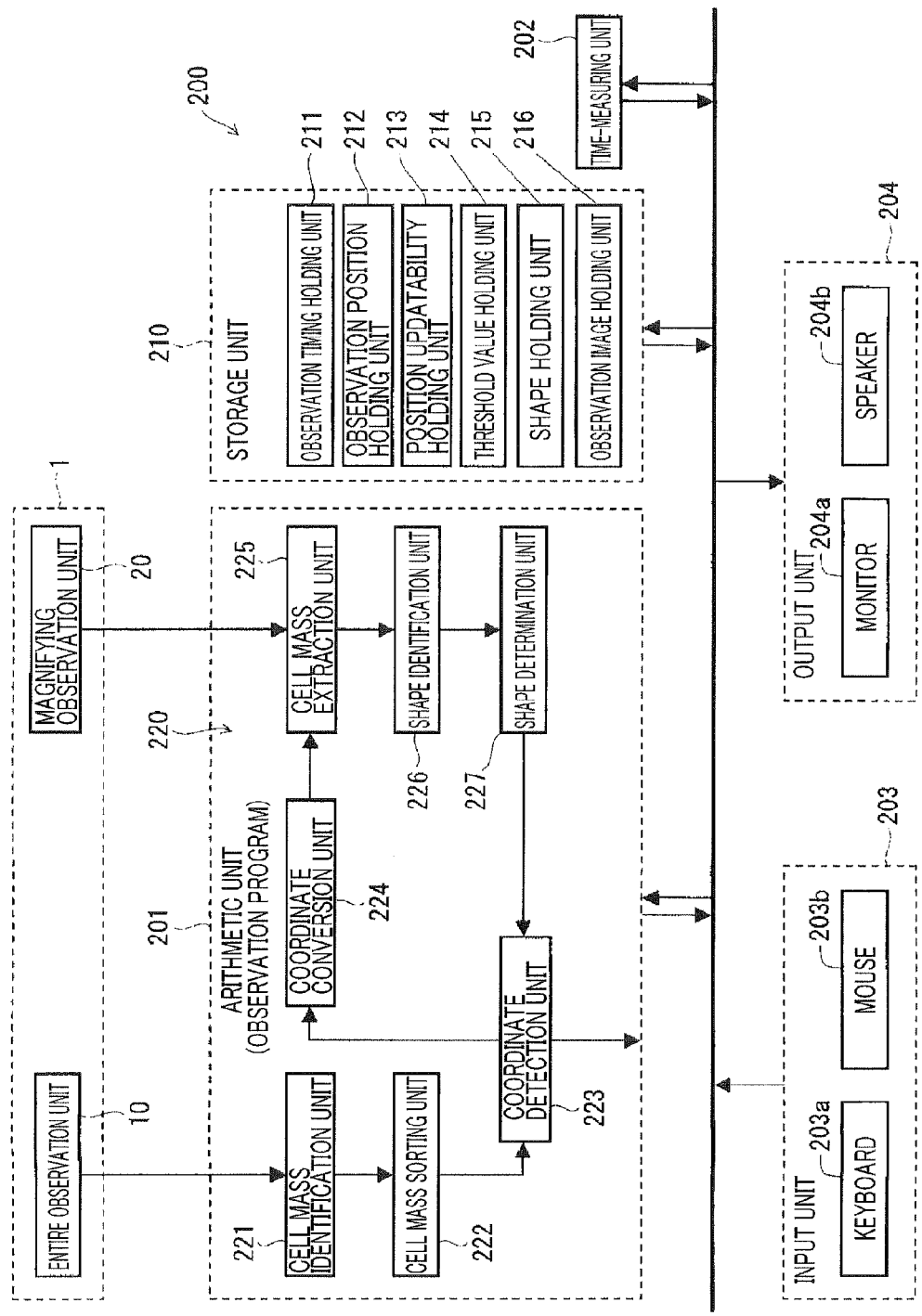
FIG. 5 is a block diagram illustrating a configuration of a computer of an observation system illustrated in FIG. 1.

First, regarding an observation system according to a first embodiment of the present invention, a configuration thereof will be described using FIGS. 1 to 5. FIG. 1 is a configuration diagram of the observation system, FIG. 2 is a perpendicular sectional side view of an observation apparatus of the observation system, FIG. 3 is a perpendicular sectional front view of the observation apparatus, FIG. 4 is a perpendicular sectional side view of the observation apparatus illustrating a state where a container has been moved to a place corresponding to an entire observation unit, and FIG. 5 is a block diagram illustrating a configuration of a computer of the observation system. In the following description, it is assumed that the x-axis direction in FIGS. 2 and 3 is a left-and-right direction, the y-axis direction is a fore-and-aft direction (+y direction to the fore and −y direction to the aft), and the z-axis direction is an up-and-down direction.

The observation system S includes an observation apparatus 1, a control device 100, and a computer 200 as illustrated in FIG. 1.

The observation apparatus 1 is a device configured to observe a sample such as a cell and connected to the control device 100. The control device 100 is a device configured to control the observation apparatus 1, and incorporates a driver, a controller, not shown, that is configured to drive the observation apparatus 1. The control device 100 is connected to the computer 200. The computer 200 is a so-called personal computer, for example, and executes an observation program, not shown, that is configured to observe the sample such as a cell. That is, the computer 200 is capable of sending an instruction to the control device 100, to control the observation apparatus 1 and perform capture, storage of images picked up during observation.

The observation apparatus 1 includes an entire observation unit 10, a magnifying observation unit 20, a conveying unit 30, and a driving unit 40 in a main body 2 that is a housing thereof as illustrated in FIGS. 1 to 4.

The observation apparatus 1 is capable of observation using the entire observation unit 10 and the magnifying observation unit 20 of a cell in a container C containing the cell and a culture fluid of the cell that is arranged at the front center part of the device. The conveying unit 30 firmly holding the container C can be moved in a desired direction such as fore-and-aft or let-and-right direction and to a desired position by the driving unit 40. The main body 2 is supported by leg portions 3 provided at 4 places to a floor surface. In the container C, a lid is provided so as to prevent contamination from the exterior of the container or contamination between itself and another container.

The entire observation unit 10 is provided at a portion on the front side of the interior of the sealed housing of the main body 2, and includes a lens 11 which is an entire observation optical system, a CMOS camera 12 which is an image pickup unit, and a ring illumination 13 which is an entire observation illumination.

The lens 11 is arranged above a movement space of the conveying unit 30 firmly holding the container C so as to be able to observe downward the container C. The CMOS camera 12 is provided vertically above the lens 11, and is arranged so that an image pickup element surface thereof is directed to the lens 11 provided below.

The ring illumination 13 has such a configuration that a plurality of LEDs attached so as to be directed diagonally upward are aligned in a ring shape and is arranged below the movement space of the conveying unit 30. A space D is provided with a predetermined distance between the ring illumination 13 and the container C of the conveying unit 30 (See FIG. 4). As a result, since a space in which air circulates is created between the ring illumination 13 and the container C, it becomes difficult to transfer heat generated by the ring illumination 13 to the container C, thereby being able to suppress an influence of heat generation caused by the ring illumination 13 upon growth of the cell. The ring illumination 13 applies light diagonally above, i.e., toward the center of the ring, and illuminates the cell in the container C as an observation target of the conveying unit 30 located above the ring illumination 13. The CMOS camera 12 and the lens 11 are arranged so that the optical axes thereof match each other, and the ring illumination 13 is arranged so that the optical axis passes through the center of the ring illumination 13.

With such a configuration, an image obtained via the lens 11 by irradiating the container C with light using the ring illumination 13 is formed on the image pickup element surface of the CMOS camera 12 in the entire observation unit 10, and by picking up an image of the entire container C, an image of the cell in the container C is picked up. Then, the picked up image is stored, thereby facilitating identification and specification of a cell mass having a plurality of cells gathering therein in the container C.

Moreover, since the entire observation unit 10 applies light diagonally above to the container C from below the container C, the light passing through a spot where the cell is present in the bottom surface of the container C is scattered by the cell, and thus a part of the scattered light enters the camera, and the cell is seen white. The light passing through a spot where no cell is present is not scattered, and thus the light does not enter the camera and the cells is seen black. As described above, it is possible to apply appropriate light for specifying the cell emerging and growing in the vicinity of the inner bottom surface of the container C. Then, such a contrast can be obtained by which the external shape of the cell can be recognized as a white mass. Irradiation of the light from below produces such an effect of preventing that the observation becomes impossible due to blown-out highlights of the cell that are caused by light reflected by the lid of the container C.

The magnifying observation unit 20 is a so-called phase-contrast microscope, provided in the rear of the entire observation unit 10 in the interior of the sealed housing of the main body 2, and includes: a magnifying observation optical system such as an objective lens 21, a reflective mirror 22, and a zoom lens 23; a CCD camera 24 which is an image pickup unit; and a phase-contrast illumination unit 25 which is a magnifying observation illumination.

The objective lens 21 is arranged immediately below the movement space of the conveying unit 30, and is provided so as to be capable of observing upward the interior of the container C. In the periphery of the objective lens 21 that is a lens unit closest to the bottom surface of the container C, an objective lens cover 26 is provided that is a cover member configured to prevent the heat generated in the lower part of the main body 2 from influencing the container C. Further, a window unit 27 is provided in an end of the upper part of the objective lens cover 26 between the objective lens 21 and the container C.

Here, the heat is generated from a motor, the camera, and the illumination in the sealed housing and filled therein, and also stays in the vicinity of the objective lens 21 and tries to radiate upward. If a cover configured to cover the entire magnifying observation optical system is used instead of the objective lens cover 26 having a small area, the proximity of the magnifying observation optical system and the bottom surface of the container C facilitates the transference of the heat in the housing, thereby facilitating increase in the temperature of the culture fluid.

In contrast thereto, in the objective lens cover 26, the area of a place close to the bottom surface of the container C is made as small as possible, thereby suppressing the influence of the heat due to no air-circulation that is caused by very little space provided between the bottom surface of the container C and the objective lens cover 26. At the same time, the objective lens cover 26 covers only the periphery of the objective lens 21, thereby being able to increase the surface area of the objective lens cover 26, and thus the heat can be scattered also in the lateral direction of the objective lens cover 26 in which the air can easily circulate, thereby being able to suppress heat transfer to the container C.

As such, by configuring the objective lens cover 26 provided, with the window unit 27 that covers only the periphery of the objective lens 21, between the magnifying observation optical system and the container C, it becomes difficult to transfer the heat generated by the magnifying observation optical system to the container C. Thus, it can be suppressed that the influence of the heat generation of the lens driving system is exerted upon the growth of the cell.

The reflective mirror 22 is arranged below the objective lens 21, and provided with such an inclination as to reflect light substantially horizontally backward. The reflective mirror 22 guides an image obtained from the objective lens 21 to the zoom lens 23 at the rear. The zoom lens 23 is arranged in such a manner as to extend in the fore-and-aft direction to the rear of the reflective mirror 22, and is configured to magnify the image obtained from the objective lens 21. The CCD camera 24 is provided in the further rear of the zoom lens 23, and is arranged such that an image pickup element surface thereof is directed toward the zoom lens 23 in the front.

The phase-contrast illumination unit 25 is provided in the upper part of the main body 2, and includes an LED 25a and a reflective mirror 25b. The LED 25a irradiates, with light, the cell to be observed in the container C of the conveying unit 30 located below the phase-contrast illumination unit 25. The reflective mirror 25b is arranged vertically above the objective lens 21, and is configured to reflect light so that the light applied by the LED 25a reaches the objective lens 21 via the container C.

With such a configuration, the magnifying observation unit 20 irradiates the container C, with light, by using the phase-contrast illumination unit 25, thereby forming an image obtained via the objective lens 21, the reflective mirror 22, and the zoom lens 23 on the image-pickup element surface of the CCD camera 24, and the area of a part in the container C is magnified, to pick up an image of the cell in the container C. Then, the picked-up image is stored, thereby facilitating identification and specification of a cell mass in the container C and close observation thereof.

In the magnifying observation unit 20, the relatively heavy magnifying observation optical system, including a plurality of the lenses and the zoom mechanisms thereof to magnify and observe the cell, is arranged in the lower part, which leads to an appropriate weight balance of the device, thereby being able to make stable magnifying observation. Further, since the objective lens 21 can be brought closer from below the container C toward the cell that emerges and grows in the vicinity of the inner bottom surface of the container C, the cell can be observed at relatively great magnification by reducing a focal distance. Further, the observation is made from below the container C in the magnifying observation unit 20, which enables observation without being affected by stains on the lid of the container C.

The conveying unit 30 is provided at the front center part of the main body 2, in such a manner as to be sandwiched by the ring illumination 13 of the entire observation unit 10 as well as the magnified observation optical system of the magnifying observation unit 20, that are disposed bellow; and the entire observation optical system of the entire observation unit 10 as well as the phase-contrast illumination unit 25 of the magnifying observation unit 20, that are disposed above. The conveying unit 30 includes a holder 31, and this holder 31 grasps the container C containing the cell to be observed and the culture fluid for the cell. The holder 31 is positioned with respect to the entire observation unit 10 and the magnifying observation unit 20, and the container C is positioned with respect to the holder 31. As a result, even if the container C and the holder 31 are removed together and the culture fluid is replaced or a reagent is charged, the same spot can be easily observed both in the entire observation unit 10 and the magnifying observation unit 20.

The driving unit 40 is provided in the rear and on the side of the conveying unit 30, and includes an x-axis driving mechanism 41, an x-axis motor 42, a y-axis driving mechanism 43, a y-axis motor 44, a z-axis motor 45, and a zoom motor 46. As illustrated in FIGS. 2 and 3, a description will be made assuming that the left-and-right direction with respect to the observation apparatus 1 is the x-axis, the fore-and-aft direction is the y-axis, and the up-and-down direction is the z-axis.

The x-axis driving mechanism 41 is arranged immediately rear of the conveying unit 30 as well as directly supports the conveying unit 30. The x-axis driving mechanism 41 includes a belt, a pulley, a slide guide member, a shaft, not shown; is driven by the x-axis motor 42; and moves the conveying unit 30 in the left-and-right direction. The y-axis driving mechanism 43 is arranged in a place on the side surface of the conveying unit 30 and the main body 2, and supports the x-axis driving mechanism 41. The y-axis driving mechanism 43 includes a belt, a pulley, a slide guide member, not shown; is driven by the y-axis motor 44; and moves the conveying unit 30 in the fore-and-aft direction together with the x-axis driving mechanism 41 (See FIG. 4).

By operating such driving mechanisms, the conveying unit 30 conveys the container C from the entire observation unit 10 to the magnifying observation unit 20 or in the opposite direction. Since the container C is moved, even if the entire observation unit 10 and the magnifying observation unit 20 are arranged at places far from each other, it becomes possible to observe the entire container C and identify an emerging cell mass, and further, magnify and observe this identified cell mass in detail.

The conveying unit 30 is configured to convey the container C in a direction orthogonal to the optical axis direction of the entire observation unit 10 and the magnifying observation unit 20 as described above, and at least one direction in the conveying directions, that is, the fore-and-aft direction is made common therebetween, thereby matching coordinates in the observation field of view in the entire observation unit 10 with coordinates in the observation field of view in the magnifying observation unit 20. Thus, the coordinates in the observation fields of view in the entire observation unit 10 and the magnifying observation unit 20 match each other, thereby being able to easily identify, using the magnifying observation unit 20, the cell mass specified through the observation of the entire container C by the entire observation unit 10. Therefore, it is prevented to erroneously identify a target cell mass, thereby being able to realize observation with high accuracy.

The z-axis motor 45 and the zoom motor 46 are arranged in the main body 2 in the rear of the conveying unit 30. The z-axis motor 45 is a motor configured to move the magnified observation optical system and the CCD camera 24 in the up-and-down direction. The zoom motor 46 is a motor configured to change a magnification of the zoom lens 23, and is capable of changing magnification of an image to be picked up.

The computer 200 includes at least an arithmetic unit 201 as illustrated in FIG. 5. The computer 200 may also include a storage unit 210, a time-measuring unit 202, an input unit 203, and an output unit 204.

The arithmetic unit 201 is constituted by a common microcomputer and other electronic components, and is configured to control a series of observation operations relating to the observation apparatus 1 on the basis of an observation program 220 and other data, etc., that are stored/inputted in/to the microcomputer, the storage unit 210, etc. An image process unit may be separately provided that is configured to execute processes of images picked up by the entire observation unit 10 or the magnifying observation unit 20.

The observation program 220 executed in the arithmetic unit 201 includes a cell mass identification unit 221, a cell mass sorting unit 222, a coordinate detection unit 223, a coordinate conversion unit 224, a cell mass extraction unit 225, a shape identification unit 226, and a shape determination unit 227 as illustrated in a hardware manner in a functional block diagram in FIG. 5. The observation program 220 executes: an entire image-pickup process of picking up an image of a cell, by sending an instruction to the entire observation unit 10 of the observation apparatus 1 and picking up an image of the entire container C; and a magnifying image-pickup process of picking up an image of a cell, by sending an instruction to the magnifying observation unit 20 and magnifying the interior of the container C, in addition to each of these process blocks.

The cell mass identification unit 221 first converts an image into a gray image if it is a color image, and then, discriminates a part that is not a cell mass and a part of a cell mass in the image picked up in the entire image-pickup process using a predetermined threshold value. As a result, binarization is executed so that the part that is not a cell mass is made into black and the cell mass part is made into white. Then, the cell, that is, the number of white pixels is calculated. A method of calculating the number of white pixels includes: a labeling method of calculating a connected region of white pixels; and a small-region method of calculating a region so that the number of white pixels in a small region, that is determined in advance at an arbitrary position, becomes as great as possible.

The labeling method is a method of identifying a cell mass by a size of a single white pixel region or the degree of density in the white pixel regions, while the small region method is a method of identifying a cell mass by the number of the white pixel regions, the range of the number thereof, and the degree of density thereof. In addition, identification may be made by the degree of isolation of the cell masses (the degree that individual cell masses exist with a predetermined distance therebetween). Here, the labeling method is employed.

The labeling process is a process of grouping a plurality of pixels by assigning the same number (label) to white pixels (or black pixels) adjacent to each other in the image subjected to the binarization process. In determination on adjacency in the labeling process, four-connection (four-neighbor) and eight-connection (eight-neighbor) are used. In the four-connection, if pixels continue up and down and right and left with respect to the pixel of interest, they are determined to be adjacent, while in the eight-connection, determination on adjacency is made considering continuation in diagonal four more directions. As such, the cell mass identification unit 221 identifies a mass of binarized white pixels, that is, a cell mass from an image picked up in the entire image-pickup process.

Then, the cell mass identification unit 221 is configured to recognize a cell mass having a size equal to or greater than a predetermined size in identified cell masses as a magnifying observation target. The "predetermined size" indicates a size set in advance for a cell mass, and of the order of such a size that can be determined to be observed under magnification. Here, the predetermined size is set at 1000 pixels for the number of pixels, for example, and is stored in the storage unit 210. As a result, a cell mass having pixels equal to or more than 1000 pixels as the number of pixels is recognized as a magnifying observation target cell mass, thereby being able to determine a time of emergence of a cell mass. Therefore, it becomes possible to perform continuous observation from a time of emergence of a cell mass to a time of completion of growth thereof.

The cell mass sorting unit 222 is configured to execute sorting of the cell masses identified by the cell mass identification unit 221, that is, masses of white pixels in order from that having the greater number of pixels. Then, the predetermined number of cell masses in order from that having the greater number of pixels, for example, is selected as observation targets.

The coordinate detection unit 223 is configured to detect coordinates of the center of a cell mass that is identified by the cell mass identification unit 221 and sorted by the cell mass sorting unit 222, that is, the mass of white pixels.

The coordinate conversion unit 224 is configured to first calculate a coordinate by a pixel on an image picked up in the entire image-pickup process. Then, the coordinate is converted into a real scale with the center of an image as the origin. Here, various aberrations such as distortion aberration of the image may be corrected. Further, the coordinate conversion unit 224 is configured to convert the real scale into the motor pulse numbers of the x-axis motor 42 and the y-axis motor 44 of the driving unit 40 in the observation apparatus 1, so as to be matched with a position on the image expressed by this real scale. As such, the coordinate conversion unit 224 is configured to form a common coordinate system in which the coordinate on the image picked up in the magnifying image-pickup process matches the coordinate on the image picked up in the entire image-pickup process.

The cell mass extraction unit 225 is configured to extract a cell mass at the coordinates detected by the coordinate detection unit 223 from the image picked up in the magnifying image-pickup process.

The shape identification unit 226 is configured to first perform matching of a patch image prepared in advance with an image picked up in the magnifying image-pickup process. As a matching result, range images, expressed by shading, of the image picked up in the magnifying image-pickup process and the patch image are obtained. Then, the shape identification unit 226 is configured to execute the binarization process for the range image using a predetermined threshold value. Matching methods includes a template matching, a histogram matching, for example, and an image to be determined, that is, an image picked up in the magnifying image-pickup process is subjected to raster scan by the patch image, thereby calculating ranges of the both. If a large number of patch images are prepared, the range images of the matching results are integrated. Even if a plurality of cell masses are present in the image picked up in the magnifying image-pickup process, the shape identification unit 226 can identify each of the cell masses separately.

Subsequently, the shape identification unit 226 detects a contour by executing contour extraction by an edge extraction filter and contour tracing by eight-connection search, for example, in an image subjected to the binarization process. As the edge extraction filter in contour extraction, a differential filter, a Prewitt filter, a Sobel filter, a Canny Edge Detector can be used, for example. In the contour tracing, a contour line can be extracted by tracing contour points sequentially in one direction from a tracing start point of a contour, and four-connection search can be also used.

Then, the shape identification unit 226 detects a predetermined shape such as a circle, an ellipse, a rectangle from the contour detection results. As a method of detecting a circle from a contour or an edge, Hough transform can be used. As a method of detecting an ellipse from a contour or an edge, a method of fitting an ellipse to a sequence of points of a contour by generalized Hough transform or least squares estimation can be used. As a method of detecting a rectangle from a contour or an edge, a method of fitting a rectangle so that all the sequences of points in a contour are included, can be used. As such, the shape identification unit 226 is configured to extract a contour of a cell mass from an image picked up in the magnifying image-pickup process and identify a shape thereof.

The shape determination unit 227 is configured to determine whether the cell mass identified by the shape identification unit 226 is in a predetermined shape. The "predetermined shape" is a shape set in advance for a cell mass, and is preferably of the order of such a shape that can be determined to have a high possibility of continuously growing in a manner suitable for observation and is close to a circle to the highest degree possible.

As the criteria for determining a predetermined shape of a cell mass, criteria such as a size and the degree of unevenness may be added to the shape, for example. The criteria for determining a shape includes the degree of ellipse of an ellipse surrounding the contour, roundness of a circle surrounding the contour, for example. The criteria for determining a size includes a size of a white pixel mass, a length of a contour of a white pixel mass, the area of the interior of a contour of a white pixel mass, a length of a long axis of an ellipse, a length of a short axis of an ellipse, a length of a circumference of an ellipse, a diameter of a circle, a length of a circumference of a circle, a length of a rectangle surrounding the contour, the area of a rectangle surrounding the contour, for example. The criteria for determining the degree of unevenness includes the ratio of the area of the contour to a peripheral length, the ratio of the area of the contour to the area of a rectangle surrounding the contour, the ratio of the length of the contour to the length of the rectangle surrounding the contour, the number of corners in a contour, the ratio of the area of the contour to the area of a circle or an ellipse surrounding the contour, the ratio of the length of the contour to the length of a circumference of a circle or a circumference of an ellipse surrounding the contour, the ratio of the area of a rectangle surrounding the contour to the area of a circle or an ellipse surrounding the contour, the ratio of the length of a rectangle surrounding the contour to the length of a circle or an ellipse surrounding the contour, for example. As a method of corner detection when determination is made on the basis of the number of corners in a contour, Harris corner detection, SUSAN operator can be used, for example.

Here, the criteria for determining the predetermined shape of a cell mass is set at the degree of ellipse equal to or smaller than 1.1, for example, and is stored in the storage unit 210. The degree of ellipse is the ratio of the long-axis length of the ellipse to the short-axis length thereof. As a result, a cell mass close to a circle to the highest degree possible is identified, thereby being able to automatically select a cell mass having an appropriate shape for continuing observation. As a result, it becomes possible to lower the observation priority of a cell mass that has grown in a distorted shape during a growing process, or stop the observation, and thus observation of a cell mass having an appropriate shape can proceed more efficiently.

Further, not only a method of explicitly determining a shape by a threshold value (e.g., the degree of ellipse of 1.1), such a method can be used that cell mass images are sorted based on superiority of determination results and displayed on a monitor 204a (in the case of the degree of ellipse, display is made in order from the smaller degree of ellipse), thereby leaving, to a user, the determination of a range in which the cell mass is considered suitable.

The storage unit 210 is configured to store various types of data relating to observation of a cell and an operation of the observation system S, and includes an observation timing holding unit 211, an observation position holding unit 212, a position updatability holding unit 213, a threshold value holding unit 214, a shape holding unit 215, and an observation image holding unit 216, for example.

The observation timing holding unit 211 is configured to hold various types of data relating to time periods and days such as a time period, the number of days, deadlines relating to observation. For example, the data includes: the "predetermined identification time period" that is a predetermined time period relating to identification of a cell mass set with respect to timing for making identification of a magnifying observation target cell mass; "the predetermined number of identification days" that is the predetermined number of days set with respect to timing for finishing identification of a magnifying observation target cell mass; the "predetermined image-pickup period" that is a predetermined time period relating to image pickup of a magnified image set with respect to timing for picking up an image of a magnified cell mass; the "predetermined observation deadline" that is a predetermined deadline set in advance with respect to timing for ending observation of a cell. These types of data are used as criteria for determination as appropriate in the observation program 220 and compared with the time periods and days measured by the time-measuring unit 202.

The observation position holding unit 212 is configured to hold data such as an observation position (coordinates) of a cell mass obtained by the entire observation, or an observation position (coordinates) set manually.

The position updatability holding unit 213 is configured to hold a flag indicating whether to update an observation position of a cell mass obtained during the previous entire observation and stored in the observation position holding unit 212, in accordance with the predetermined identification time period stored in the observation timing holding unit 211.

The threshold value holding unit 214 is configured to hold various types of data relating to a threshold value with respect to observation. For example, the data includes: a threshold value for determining whether it is a white pixel or a black pixel during the binarization process; a threshold value relating to the number of pixels for determining whether to extract the labeled white pixel cell mass as a cell mass.

Further, the threshold value holding unit 214 is configured to hold a threshold value for identifying a cell mass capable of growing in a favorable manner, when shape identification process is executed. For example, such data includes: a threshold value of the number of pixels for determination by the size of a white pixel mass; a threshold value of the length of a contour for determination by the length of the contour of the white pixel mass; a threshold value of an area for determination by the area of the interior of the contour of the white pixel mass; a threshold value of roundness for determination by the roundness of a circle surrounding the contour; a threshold value of the ratio of an ellipse long axis to an ellipse short axis for determination by the degree of ellipse of an ellipse surrounding the contour; a threshold value of a diameter for determination by the diameter of a circle; a threshold value of a circumference for determination by the length of a circumference; a threshold value of a long axis for determination by a long-axis length of an ellipse; a threshold value of a short axis for determination by a short-axis length of an ellipse; a threshold value of an ellipse circumference for determination by the length of a circumference of an ellipse; a threshold value of a length of a rectangle for determination by the length of the rectangle surrounding the contour; a threshold value of the area of a rectangle for determination by the area of the rectangle surrounding the contour; a threshold value of the ratio of the area of the contour to the peripheral length for determination by the ratio of the area of the contour to the peripheral length; a threshold value of the area ratio for determination by the ratio of the area of the contour to the area of the rectangle surrounding the contour; a threshold value of the length ratio for determination by the ratio of the length of the contour to the length of the rectangle surrounding the contour; a threshold value of the number of corners for determination by the number of corners of a contour; a threshold value of the area ratio for determination by the ratio of the area of the contour to the area of a circle or an ellipse surrounding the contour; a threshold value of the length ratio for determination by the ratio of the length of the contour to the length of a circle or an ellipse surrounding the contour; a threshold value of the area ratio for determination by the ratio of the area of the rectangle surrounding the contour to the area of a circle or an ellipse surrounding the contour; and a threshold value of the length ratio for determination by the ratio of the length of the rectangle surrounding the contour to the length of a circle or an ellipse surrounding the contour.

The shape holding unit 215 is configured to hold a shape identification process result of a cell mass for all the methods of the shape identification process.

The observation image holding unit 216 is configured to hold magnified observation images and entire observation images.

The observation timing holding unit 211 and the threshold value holding unit 214 also function as a setting unit by which a user can change various settings relating to the observation program 220 as appropriate. The setting matters that can be set using the observation timing holding unit 211 include: timing for picking up an image in the entire observation unit 10 or the magnifying observation unit 20; and the time period, the number of days, the deadline relating to the observation, for example. The setting matters that can be set using the threshold value holding unit 214 include: the predetermined size of a cell mass that is a determination standard of a magnifying observation target cell mass; a predetermined shape of a cell mass that is a determination standard on whether the cell mass is in an appropriate shape for continuing observation, for example.

The time-measuring unit 202 is configured to measure time relating to time periods and days from start of observation of a cell and operation control of the observation system S, thereby being able to grasp various types of time.

The input unit 203 includes pointing devices such as a keyboard 203a, a mouse 203b, for example. The user inputs characters, numerical values by using the keyboard 203a. Further, the user moves a cursor in an arbitrary direction on a screen of the monitor 204a of the output unit 204 by using the mouse 203b, and selects a menu or other options. The arithmetic unit 201 is configured to execute various types of processes to a program, data, and a file stored/inputted in/to the arithmetic unit 201 and the storage unit 210 on the basis of information obtained from the input unit 203, and execute an output process to the output unit 204.

The output unit 204 includes: the monitor 204a such as a liquid crystal display, a CRT; and a speaker 204b, for example. The arithmetic unit 201 is configured to cause a window, an icon, a menu to be displayed on the monitor 204a on the basis of the executed process of a program, and cause sound to be emitted from the speaker 204b. Further, the arithmetic unit 201 is configured to cause characters, numerical values inputted by the user to be displayed on the monitor 204a on the basis of the information from the input unit 203, and cause a cursor that is to be moved by the user to be displayed.

Figure 6:
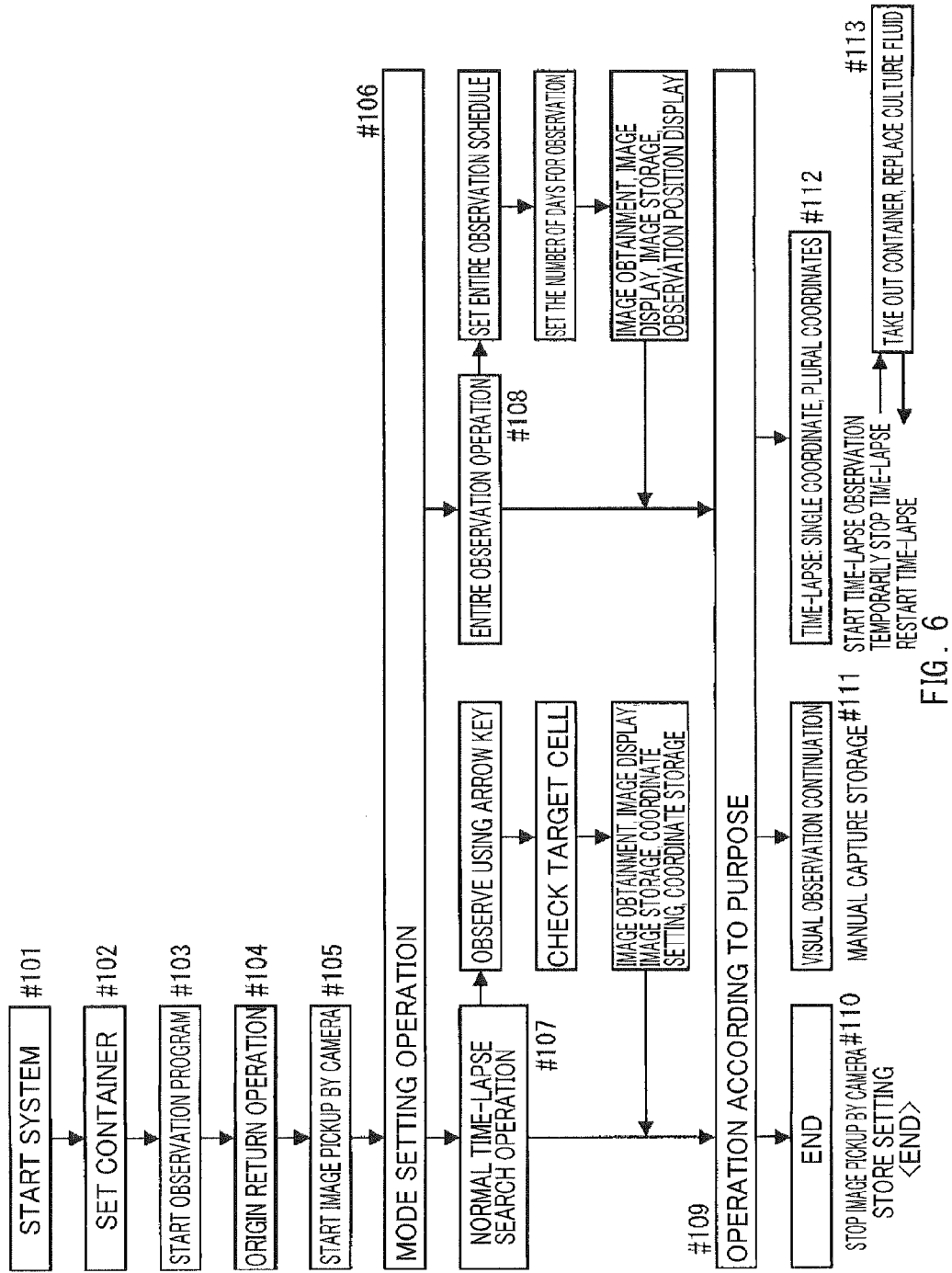
FIG. 6 is an explanatory diagram illustrating a flow according to an operation of an observation system in FIG. 1.

Subsequently, an operation of the observation system S by the user relating to observation of a cell in the container C will be described along a flow illustrated in FIG. 6. FIG. 6 is an explanatory diagram illustrating the flow relating to an operation of the observation system S.

The user first turns on the observation apparatus 1, the control device 100, and the computer 200, thereby starting the observation system S (Step #101 in FIG. 6). Then, the user sets the container C containing a cell and a culture fluid for the cell on the holder 31 of the conveying unit 30 (Step #102). Subsequently, the user starts the observation program 220 in the computer 200 (Step #103), and then an operation screen is displayed on the monitor 204a.

The observation program 220 is executed to perform an origin return operation of the conveying unit 30 automatically together with startup of the program (Step #104). Then, the observation program 220 is executed to start image pickup by a camera (Step #105), and display a real-time image from the camera on the monitor 204a.

Subsequently, the user executes a mode setting operation (Step #106). In this mode setting operation, a normal time-lapse search operation (Step #107) and an entire observation operation (Step #108) can be selected. The time lapse observation is a method of observing a position, set in advance, in every predetermined time period.

In the normal time-lapse search operation (Step #107), the user observes the interior of the container C while moving the container C using an arrow key on the monitor 204a or the keyboard 203a, and checks a target cell. Then, the user executes acquisition, display and storage of a captured image, and further setting of coordinates, storage of the coordinates.

In the entire observation operation (Step #108), the user sets the predetermined identification time period and the predetermined number of days for identification in the entire observation. The acquisition, display and storage of the image and further observation position display are automatically executed on the basis of the setting.

Subsequently, in an operation according to purpose (Step #109), a choice can be made from operations of end (Step #110), visual observation continuation (Step #111), and the time lapse (Step #112).

If the end (step #110) is selected, the image pickup by the camera is stopped, and the setting is stored. If the visual observation continuation (Step #111) is selected, manual capture storage of an image picked up by the camera can be performed.

If the time-lapse (Step #112) is selected, operations of start of the time-lapse observation, time-lapse temporary stop, and time-lapse restart can be performed. If the time lapse is temporarily stopped, works such as taking-out of the container C, replacement of the culture fluid can be performed (Step #113).

By performing the time-lapse observation by using such observation program 220, it is possible to automatically execute such a series of processes that a cell mass having emerged is identified in an image picked up in the entire image-pickup process and the position thereof is specified; and a shape of the cell mass is identified from an image picked up in the magnifying image-pickup process and a cell mass in an appropriate shape for continuing the observation is selected.

Figure 7:
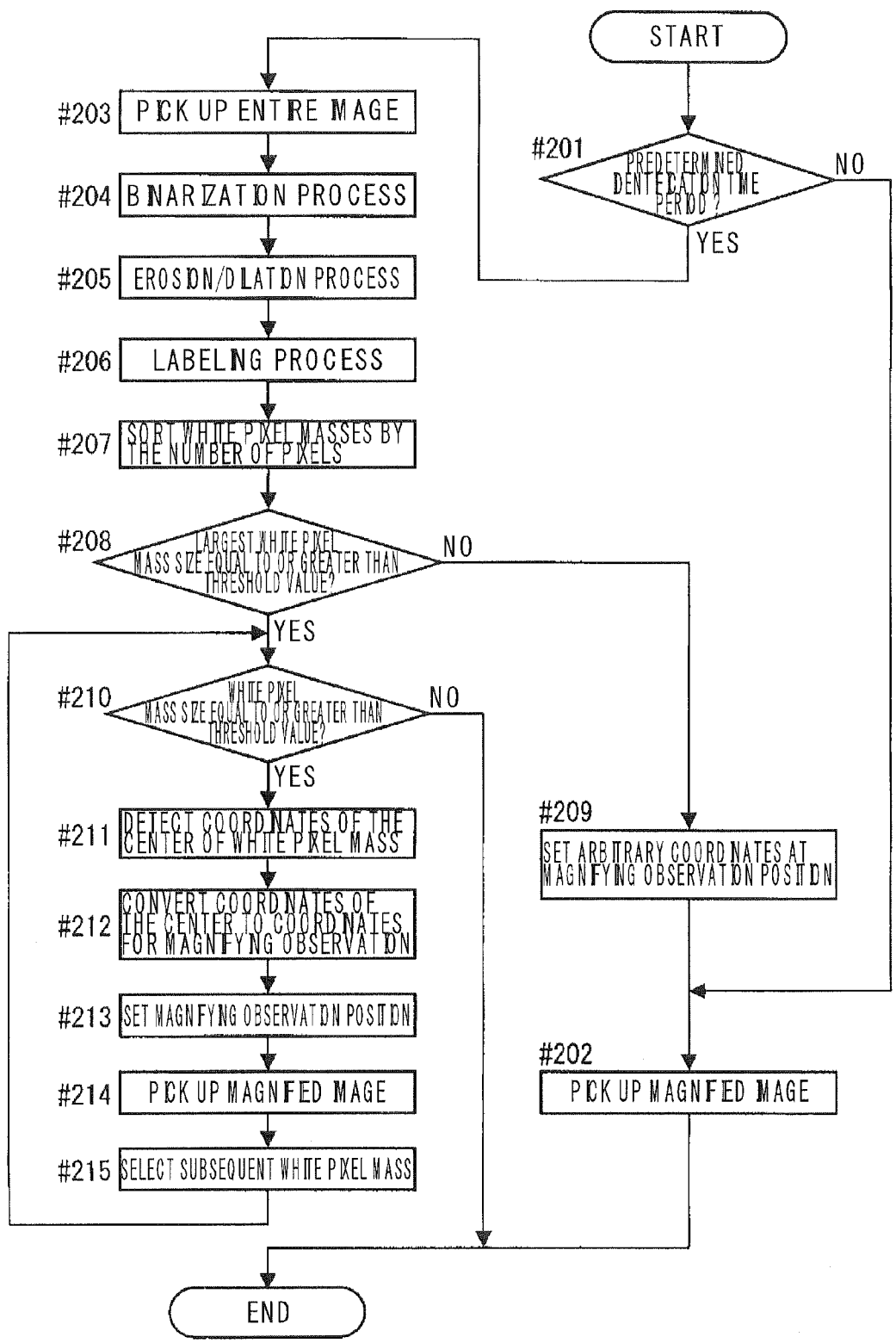
FIG. 7 is a flowchart illustrating an operation according to an observation process in an observation system in FIG. 1.

Subsequently, an operation relating to the observation process in the observation system S will be described along a flow illustrated in FIG. 7. FIG. 7 is a flowchart illustrating the operation relating to the observation process in the observation system S.

If the observation program 220 is executed (Start in FIG. 7), the observation 220 is first executed to determine whether it is in the predetermined identification time period (Step #201). With respect to this, the observation program 220 is executed to cause the time-measuring unit 202 to measure, in advance, time periods and days from start of the observation of a cell after seeding thereof and a time period from the previous identification of the magnifying observation target cell mass by using the magnifying observation unit 20, for example. The predetermined identification time period is a time period set in advance with respect to timing for making identification of the magnifying observation target cell mass, and it is set at one day, for example, and stored in the observation timing holding unit 211 of the storage unit 210. The predetermined identification time period can be set as appropriate.

If it is not in the predetermined identification time period at Step #201 (No at Step #201), the observation program 220 causes the magnifying observation unit 20 to pick up a magnified image (Step #202), and causes the flow of the operations relating to the observation process to be ended (End in FIG. 7).

Whereas, if it is in the predetermined identification time period at Step #201 (Yes at Step #201), the observation program 220 is executed to send an instruction to the entire observation unit 10 of the observation apparatus 1 to pick up an image of the entire container C, thereby picking up an image of a cell (Step #203). Subsequently, the observation program 220 is executed to perform the binarization process of discriminating between a portion that is not a cell mass and a portion that is a cell mass in the picked-up entire image by using a predetermined threshold value (Step #204). As a result, binarization is performed such that the portion that is not a cell mass is converted into black and the portion of the cell mass is converted into white.

Further, the observation program 220 is executed to perform erosion/dilation process (Step #205). The erosion/dilation process includes: an erosion process that is a process of taking off a white pixel in contact with a black pixel; and to the contrary, a dilation process that is a process of adding a white pixel in contact with the black pixel. In the erosion process, a mass of micro white pixels can be reversed to black pixels, while in the dilation process, a mass of micro black pixels present in a white pixel region can be reversed to white pixels, thereby exerting an effect of removing noise.

Then, the observation program 220 is executed to execute the labeling process (Step #206), calculate the number of white pixels in each small region at an arbitrary position set in advance, and identify a mass of white pixels, that is, a cell mass. Further, the observation program 220 is executed to perform sorting in order from a cell having the greater number of pixels in the identified cell masses, that is, the masses of white pixels (Step #207).

Subsequently, the observation program 220 is executed to determine whether the largest mass of white pixels (cell mass) is of a size having a threshold value, that is, a size equal to or greater than the predetermined size (Step #208). This predetermined size serving as a threshold value is set at 1000 pixels for the number of pixels, for example, and is stored in the threshold value holding unit 214 of the storage unit 210. If the largest cell mass is of a size smaller than the predetermined size (No at Step #208), the observation program 220 is executed to detect arbitrary coordinates of an entire image picked up by the entire observation unit 10, set it as a magnifying observation position (Step #209), and cause the magnifying observation unit 20 to pick up a magnified image (Step #202). Then, the observation program 220 is executed to finish a flow for the operations relating to the observation process (End in FIG. 7).

Whereas, if the largest cell mass is of a size equal to or greater than the predetermined size at Step #208 (Yes at Step #208), the observation program 220 is executed to determine again whether the cell mass selected is of a size equal to or greater than the predetermined size (Step #210). If the cell mass is of a size equal to or greater than the predetermined size (Yes at Step #210), the observation program 220 is executed to recognize the mass of white pixels (cell mass) as a magnifying observation target cell mass, and detect the coordinates of the center thereof (Step #211). Further, the observation program 220 is executed to convert the coordinates of the center thereof into the coordinates for observation of a magnified image (Step #212).

Subsequently, the observation program 220 is executed to set the converted coordinates of the center of the cell mass as a magnifying observation position (Step #213), and causes the magnifying observation unit 20 to pick up a magnified image (Step #214). Then, the observation program 220 is executed to select the subsequent mass of white pixels (cell mass) as a target to be determined on whether or not it is a magnifying observation target cell mass (Step #215), and return to Step #210 to determine whether or not the cell mass is of a size equal to or greater than the predetermined size.

Until the cell mass identified at Step #206 becomes of a size smaller than the predetermined size (No at Step #210), the flow from Step #210 to Step #215 is repeated, and the magnifying observation position of the cell mass recognized as the magnifying observation target is set continuously. When the cell mass identified at Step #206 is of a size smaller than the predetermined size (No at Step #210), the observation program 220 is executed to end the flow for the operations relating to the observation process (End in FIG. 7).

In the time-lapse observation, a position of a cell mass that is to become a magnifying observation target is set manually by the user, or position setting (position specification) of the cell mass is performed from an entire observation result. For the cell mass whose position has been specified, the observation program 220 is executed to send an instruction to the magnifying observation unit 20 in every predetermined image-pickup period, so that the interior of the container C is magnified and an image of the cell is picked up, and the image pickup is stopped on condition that the predetermined observation deadline is reached.

The predetermined observation deadline is a deadline set in advance with respect to timing for finishing the observation of a cell, and is set at 10 days, for example, and stored in the observation timing holding unit 211. The predetermined observation deadline can be set as appropriate.

As such, from the image obtained by picking up an image of the entire container C, the cell mass is identified and the coordinates thereof are detected, and then magnification is performed with the detected coordinates as the center of magnification, thereby being able to observe the details of the cell mass. Further, the image of a magnified cell is picked up in every predetermined image-pickup period, and when reaching the observation deadline, the image pickup is finished, thereby being able to perform the time-lapse observation continuously from a time of emergence of a cell mass to a time of completion of growth thereof.

According to the configuration of an embodiment of the present invention, in observing a cell being cultured in the container C, it becomes possible to provide the observation apparatus 1 capable of specifying a cell mass having emerged by observing the entire container C, and observe the details of the specified cell mass by magnifying it. Further, it becomes possible to provide the observation program 220, the observation method, and the observation system S capable of continuous observation of such a specified cell mass from a time of emergence to a time of completion of growth thereof.

<Second Embodiment>

Figure 8:
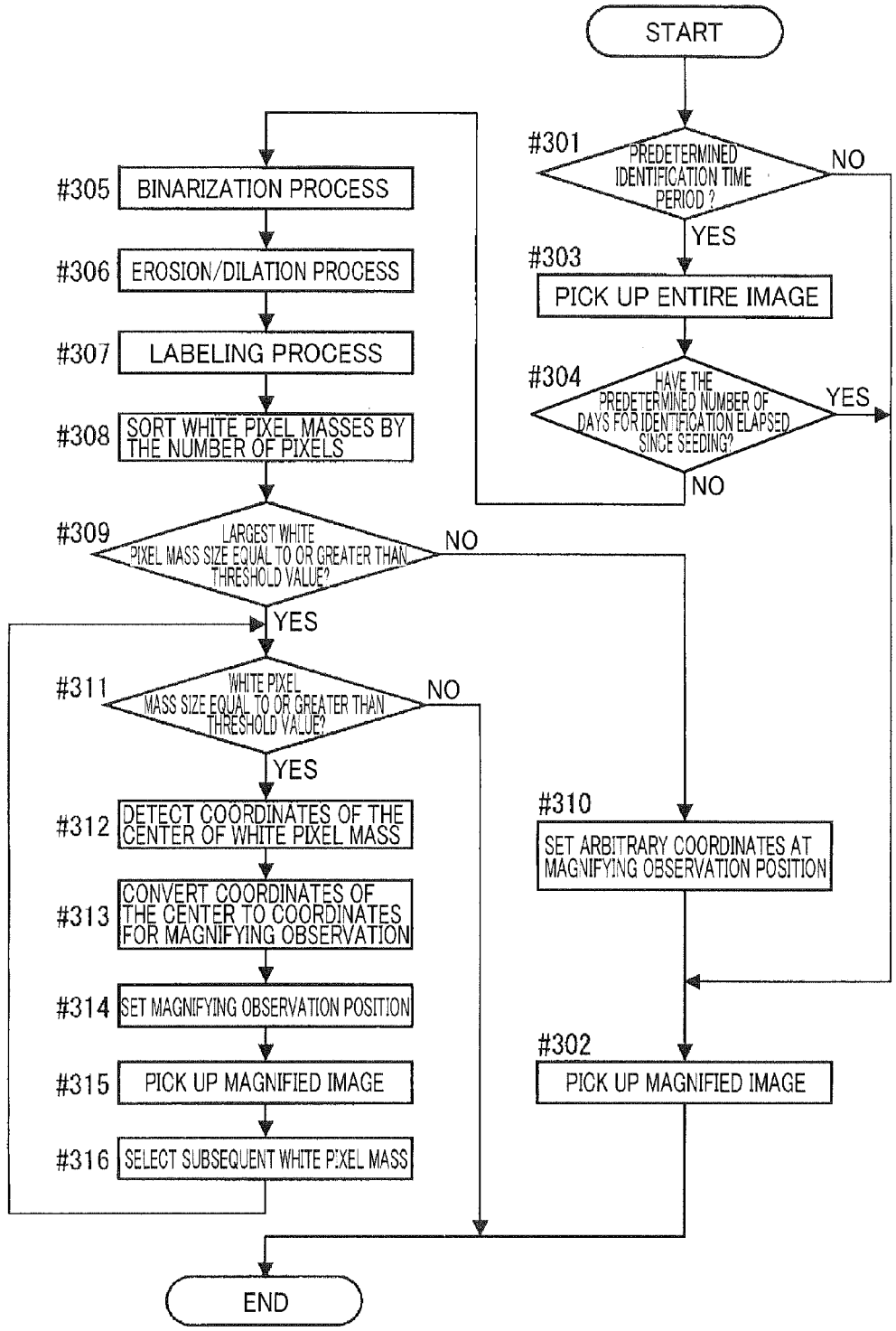
FIG. 8 is a flowchart illustrating an operation according to an observation process in an observation program according to a second embodiment.

Subsequently, a description will be given, referring to a flow illustrated in FIG. 8, of an operation in an observation process regarding an observation program according to a second embodiment of the present invention. FIG. 8 is a flowchart illustrating the operation relating to the observation process in the observation program. Since the basic configuration of this embodiment is the same as that of a first embodiment of the present invention described by using FIGS. 1 to 7, illustration and description of the constituent elements equivalent to those illustrated in a first embodiment of the present invention will be omitted.

When the observation program 220 according to a second embodiment of the present invention is executed (Start in FIG. 8), the observation program 220 is first executed to determine whether it is in the predetermined identification time period (Step #301). When it is in the predetermined identification time period (Yes at Step #301), the observation program 220 is executed to send an instruction to the entire observation unit 10 of the observation apparatus 1, and cause an image of a cell to be picked up by picking up an image of the entire container C (Step #303).

Subsequently, the observation program 220 is executed to determine whether or not the predetermined number of days for identification has elapsed since seeding of a cell in the container C (Step #304). With respect to this, the observation program 220 is executed to cause the time-measuring unit 202 to measure, in advance, time periods and days from start of the observation of the cell, for example, after the seeding thereof. The predetermined number of days for identification is the number of days set in advance with respect to timing for finishing identification of the magnifying observation target cell mass, is set at five days, for example, and is stored in the observation timing holding unit 211 of the storage unit 210.

At Step #304, if five days, which are the predetermined number of days for identification after the seeding, have elapsed as the time periods and days from start of the observation of the cell, for example (Yes at Step #304), the observation program 220 is executed to cause the magnifying observation unit 220 to pick up a magnified image (Step #302), and finish a flow for the operations relating to the observation process (End in FIG. 8). That is, if five days have elapsed since start of observation, identification of a cell mass to be a magnifying observation target is stopped, and the positional information is not updated.

At Step #304, if five days, which are the predetermined number of days for identification after the seeding has not elapsed as the time periods and days from start of the observation of the cell, for example (No at Step #304), the observation program 220 is executed to execute the binarization process of discriminating between a portion that is not a cell mass and a portion that is a cell mass in a picked up entire image by using the predetermined threshold value (Step #305). Hereinafter, since the operation flow from Step #305 to Step #316 is equivalent to the operation flow from Step #204 to Step #215 in a first embodiment of the present invention, the description thereof will be omitted.

Then, in the time-lapse observation, identification of the magnifying observation target cell mass described above is repeated until the magnifying observation target cell mass can be recognized in every predetermined identification time period, and the identification of the magnifying observation target cell mass is stopped on the condition that the predetermined number of days for identification (five days) has elapsed. The predetermined identification time period is a time period measured by the time-measuring unit 202 that is set in advance with respect to timing for executing the identification of the magnifying observation target cell mass, and is set at one day, for example, and stored in the observation timing holding unit 211 of the storage unit 210. The predetermined identification time period and the predetermined number of days for identification can be set as appropriate.

As such, the identification of the magnifying observation target cell mass is repeated every predetermined identification time period (one day) until the magnifying observation target cell mass is recognized, that is, a time of emergence of the cell mass is determined, thereby being able to automatically determine a time of emergence of a cell mass. Further, the identification of the magnifying observation target cell mass is stopped after the predetermined number of days for identification (five days) has elapsed from the start of the observation of the cell, thereby being able to perform only the magnifying observation of the cell mass specified in the entire observation and efficiently proceed with observation until completion of growth thereof.

The determination on whether to continue the identification of the magnifying observation target cell mass may be performed by a method of leaving such determination to a user by providing a window or a user interface through which the user can make setting freely, in addition to a method of automatically performing determination based on the number of days as Step #304.

<Third Embodiment>

Figure 9:
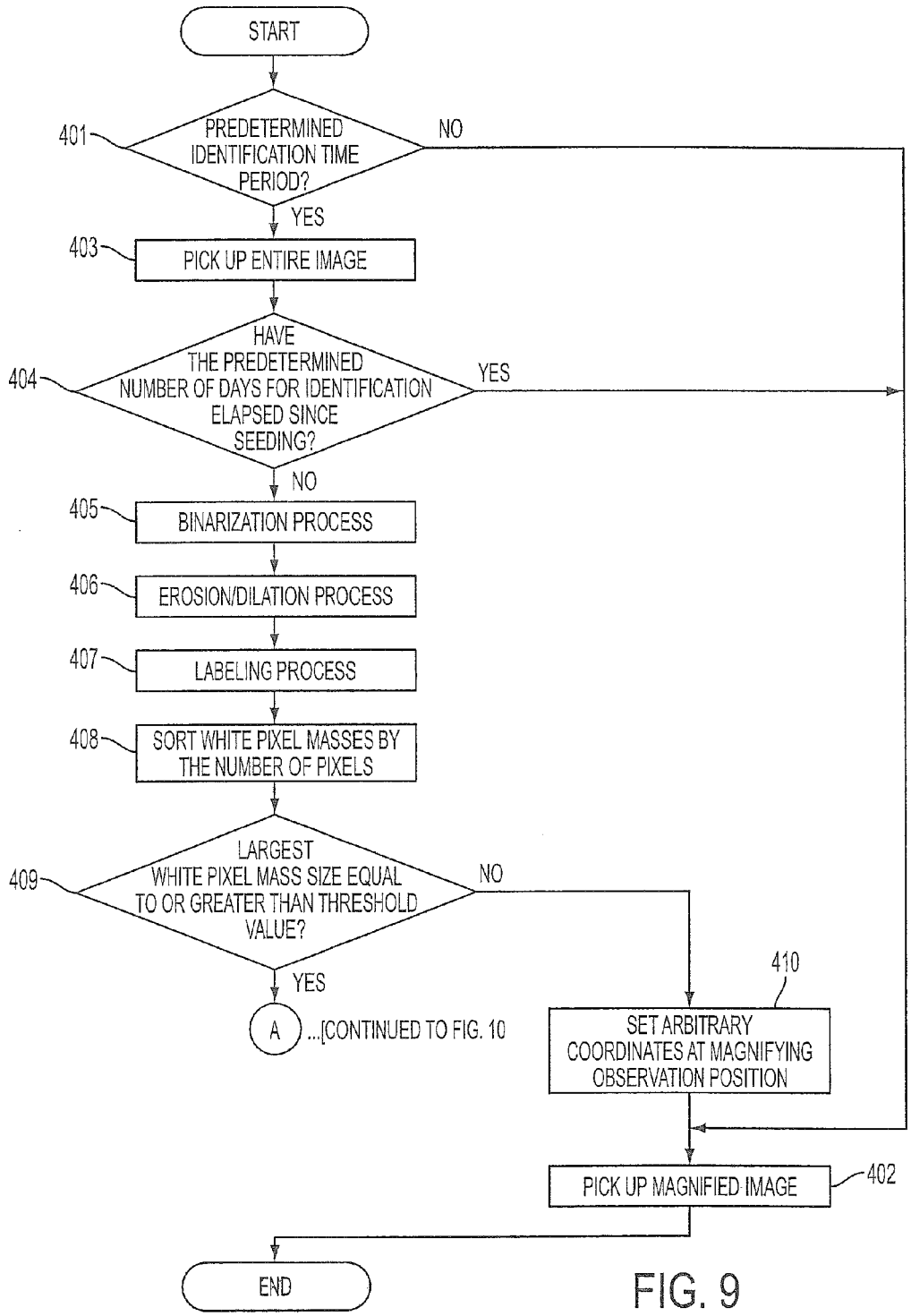
FIG. 9 is a flowchart illustrating an operation according to an observation process in an observation program according to a third embodiment.
Figure 10:
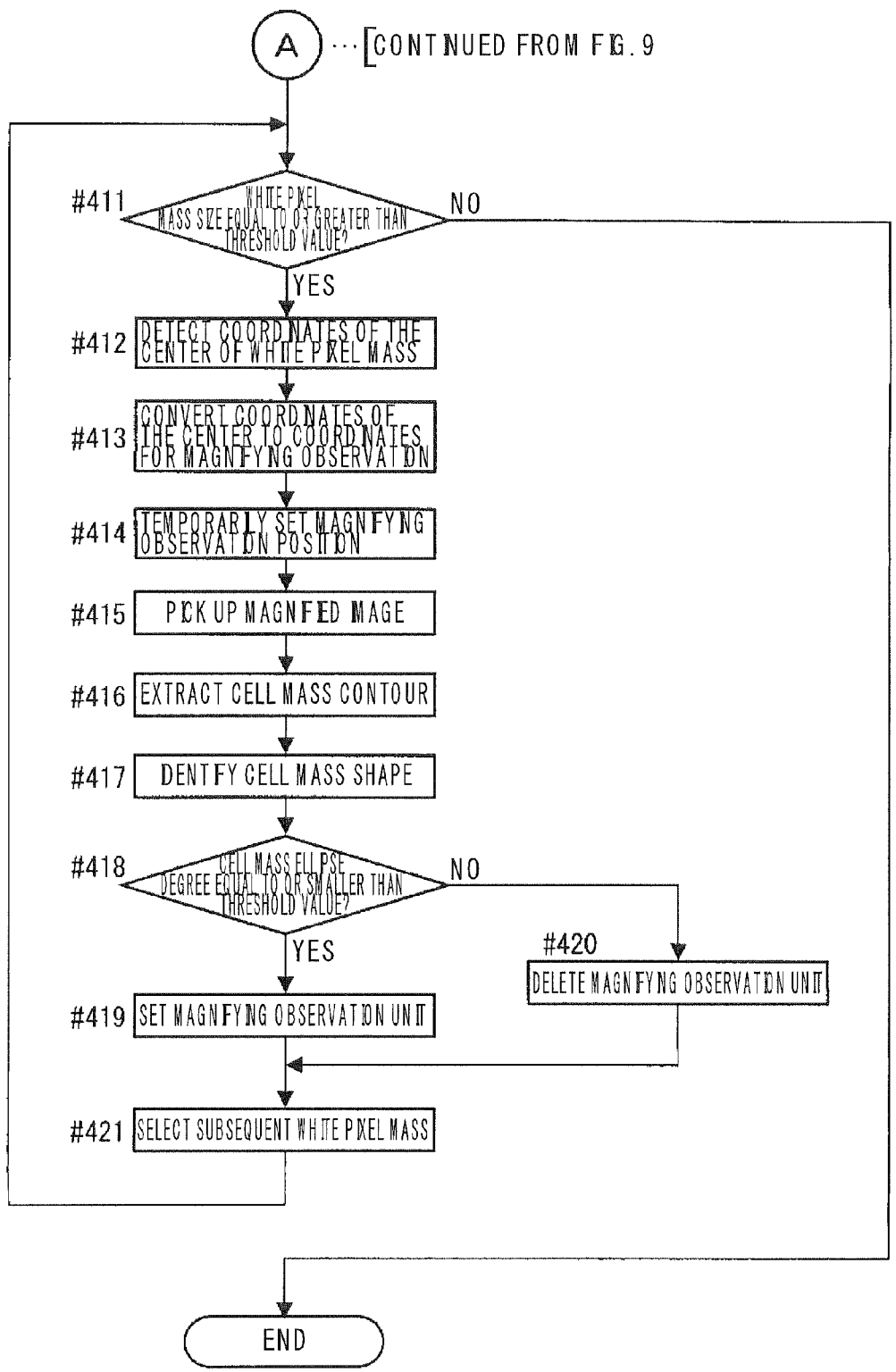
FIG. 10 is a continuation of a flowchart illustrating an operation according to an observation process illustrated in FIG. 9.

Subsequently, a description will be given, referring to a flow illustrated in FIGS. 9 and 10, of an operation in an observation process regarding an observation program according to a third embodiment of the present invention. FIG. 9 is a flowchart illustrating an operation relating to the observation process in the observation program, and FIG. 10 is a continuation of the flowchart illustrating the operation relating to the observation process illustrated in FIG. 9. Since the basic configuration of an embodiment of the present invention is the same as those of first and second embodiments of the present invention, illustration and description of the constituent elements equivalent to those illustrated in first and second embodiments of the present invention will be omitted.

In a third embodiment of the present invention, since the operation flow from Step #401 to Step #410 in FIG. 9 and the operation flow from step #411 to Step #413 in FIG. 10 are the same as the operation flows in FIGS. 7 and 8, the descriptions thereof will be omitted.

The observation program 220 is executed to temporarily set the coordinates of the center of the cell mass coordinate-converted for magnifying observation at Step #413 in FIG. 10 as a magnifying observation position (Step #414). Then, the observation program 220 is executed to send an instruction to the magnifying observation unit 20, cause the magnifying observation unit 20 to perform magnification with respect to the magnifying observation position in the container C, and pick up an image of the cell (Step #415).

Subsequently, the observation program 220 is executed to extract a contour of a cell mass from an image picked up in the magnifying image-pickup process (Step #416), and identify the shape (Step #417). Then, the observation program 220 is executed to determine whether or not the identified cell mass is in a predetermined shape, that is, the cell mass has the degree of ellipse equal to or smaller than the threshold value (Step #418). The degree of ellipse of the threshold value indicating this predetermined shape is set at 1.1, for example, and is stored in the threshold value holding unit 214 in the storage unit 210. The degree of ellipse of the threshold value indicating the predetermined shape of the cell mass can be set as appropriate. Further, other criteria for determining the predetermined shape of the cell mass, such as roundness, can be also set in place of the degree of ellipse.

At Step #418, if the degree of ellipse of the cell mass is equal to or smaller than the threshold value (Yes at Step #418), the observation program 220 is executed to formally set the coordinates of the center of the cell mass as a magnifying observation position (Step #419). Whereas, if the degree of ellipse of the cell mass exceeds the threshold value (No at Step #418), the observation program 220 is executed to delete the temporarily set magnifying observation position (Step #420). Then, the observation program 220 is executed to select the subsequent mass of white pixels (cell mass) as a target to be determined on whether it is the magnifying observation target cell mass (Step #421), return to Step #411, and determine whether or not the selected cell mass is of a size equal to or greater than the predetermined size.

As such, since the cell mass in a predetermined shape is identified, a cell mass in an appropriate shape for continuing observation can be automatically selected. As a result, observation of a cell mass having grown to a distorted shape during the growing process can be stopped, and observation of a cell mass having an appropriate shape can proceed more efficiently.

The determination of the shape of the cell mass at Step #418 may be made not only by an explicit method using a threshold value (the degree of ellipse of 1.1, for example), but also such a method may be used that cell mass images are sorted on the basis of superiority of determination results and displayed on the monitor 204a (in the degree of ellipse, display is made in order from the smaller degree of ellipse), thereby leaving, to a user, the determination of a range in which a cell mass is considered suitable.

<Fourth Embodiment>

Subsequently, an operation in an observation process regarding an observation program according to a fourth embodiment of the present invention will be described along a flow illustrated in FIG. 11 referring to FIGS. 12 to 21 as appropriate. Since the basic configuration according to this embodiment of the present invention is the same as those of first to third embodiments of the present invention, illustration and description of the constituent elements equivalent to those illustrated in first to third embodiments of the present invention will be omitted.

Figure 12:
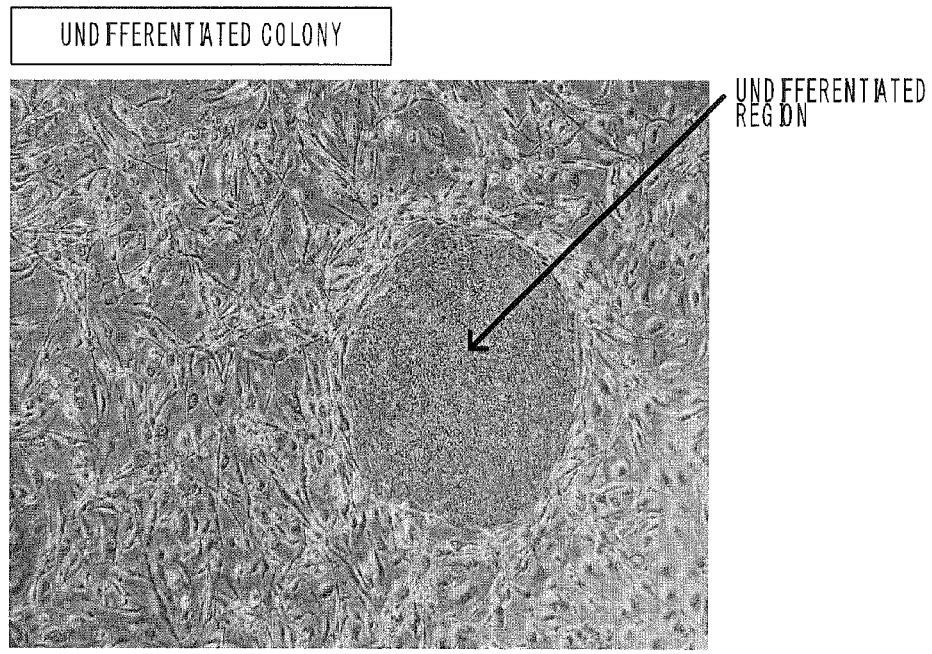
FIG. 12 is a diagram illustrating an undifferentiated colony as an example of a cell mass having an appropriate shape for continuing observation.

In maintenance and culture of iPS cell, differentiated colonies are removed, in which a state of cell groups has been changed (differentiated) in the center part or peripheral part, and only undifferentiated colonies are continuously cultured. For example, an undifferentiated colony illustrated in FIG. 12 is constituted by only undifferentiated regions, while a differentiated colony (hereinafter referred to as a differentiated colony 1) illustrated in FIG. 13 has a differentiated region generated in the center part of the colony. Thus, the observation program according to an embodiment of the present invention is executed to select the undifferentiated colony as a cell mass having an appropriate shape for continuing observation as a target of magnifying observation, and not to perform magnifying observation for the differentiated colonies.

Figure 11:
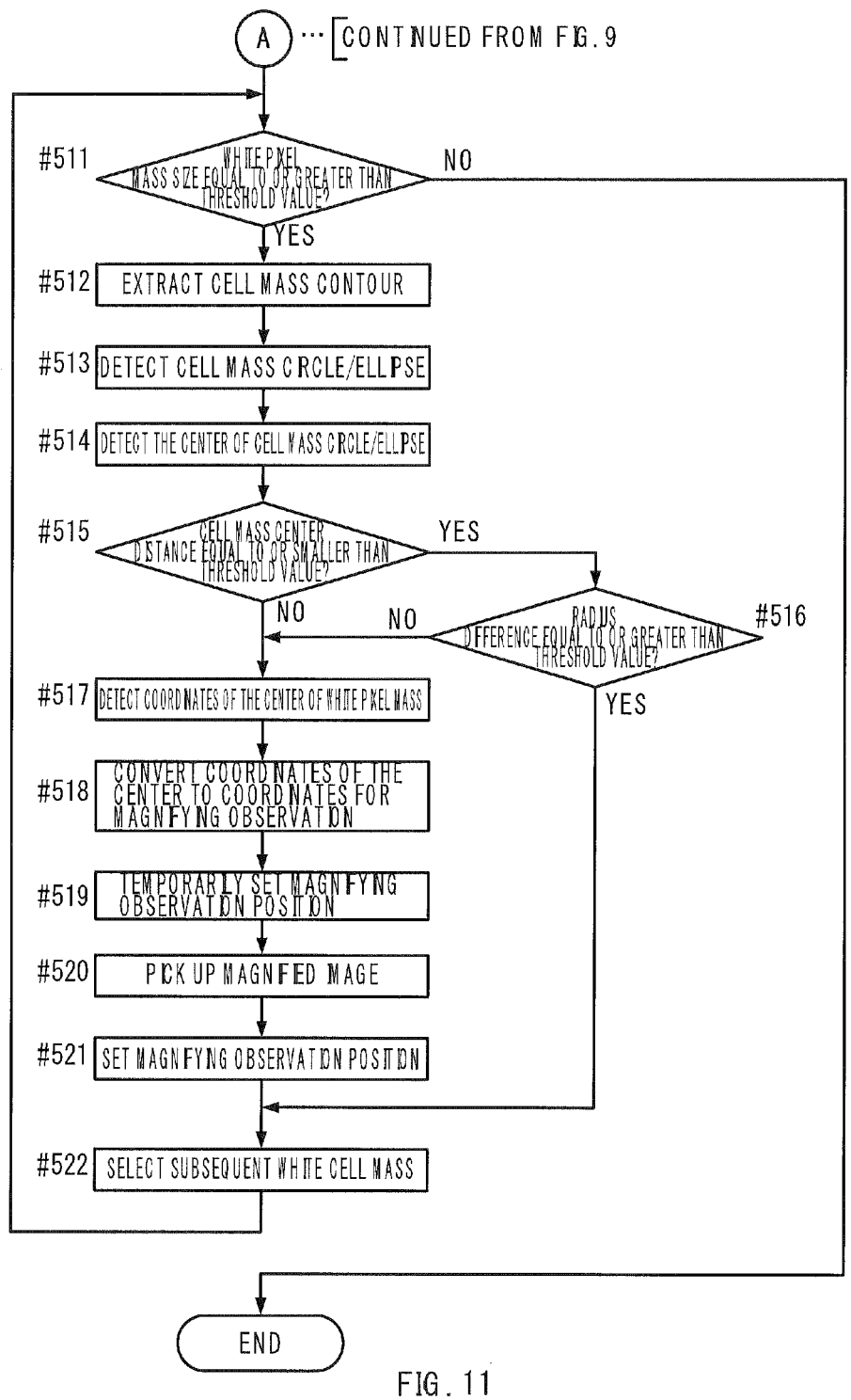
FIG. 11 is a flowchart illustrating an operation according to an observation process in an observation program according to a fourth embodiment.

FIG. 11 is a flowchart illustrating an operation relating to the observation process in the observation program and is a continuation of the flowchart illustrating the operation relating to the observation process illustrated in FIG. 9. Thus, the observation program according to an embodiment of the present invention includes the operation flow from Step #401 to Step #410 in FIG. 9 and the operation flow from Step #511 to Step #522 in FIG. 11. The description of the operation flow from Step #401 to Step #410 in FIG. 9 that is common with a third embodiment of the present invention will be omitted.

At Step #511, similarly to Step #210 in a first embodiment of the present invention, the observation program 220 is executed to determine whether the selected cell mass is of a size equal to or greater than a predetermined size. If the cell mass is of a size equal to or greater than the predetermined size (Yes at Step #511), the observation program 220 is executed to execute contour extraction by using the above-described edge extraction filter, contour tracing by using eight-connection search, for example, so as to extract a contour of the cell mass (Step #512). Further, the observation program 220 is executed to detect a circle or an ellipse from the extracted figure of the contour by using the above-described Hough transform, generalized Hough transform, for example (Step #513) and further detect the center thereof (Step #514).

Figure 13:
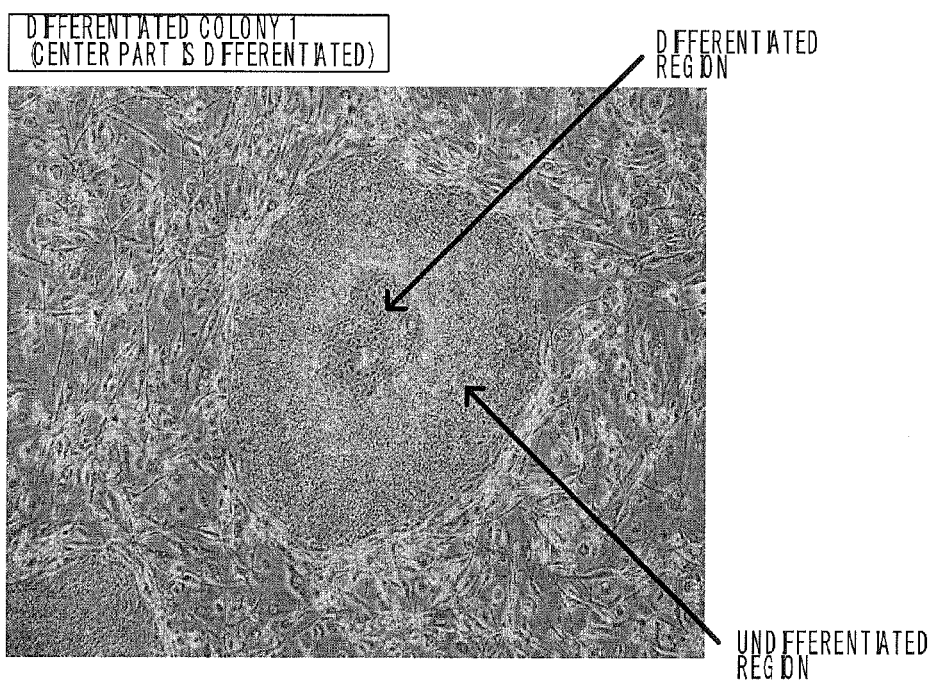
FIG. 13 is a diagram illustrating a differentiated colony whose center part is differentiated as an example of a cell mass having a shape inappropriate for continuing observation.
Figure 14:
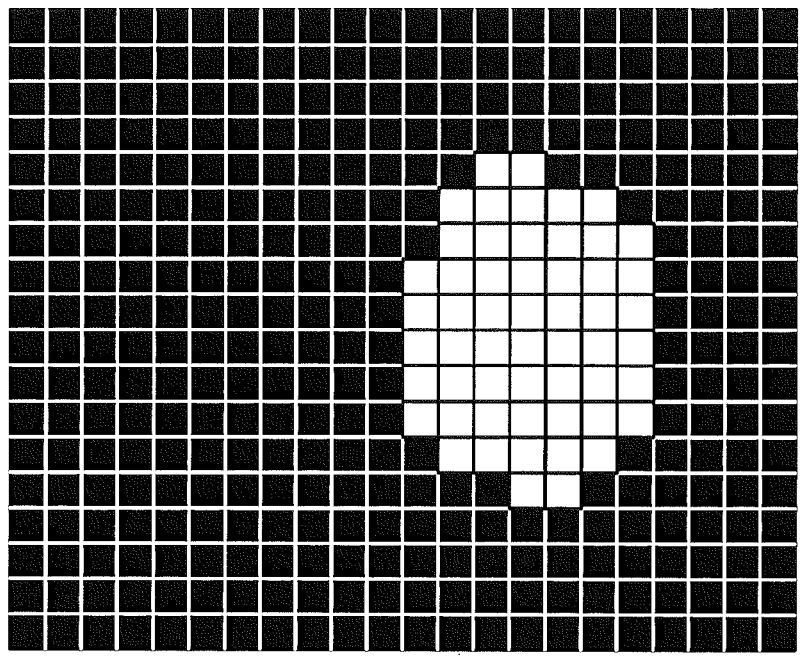
FIG. 14 is a diagram illustrating an example of a result obtained by applying a binarization process and an erosion/dilation process to an image of an undifferentiated colony.
Figure 15:
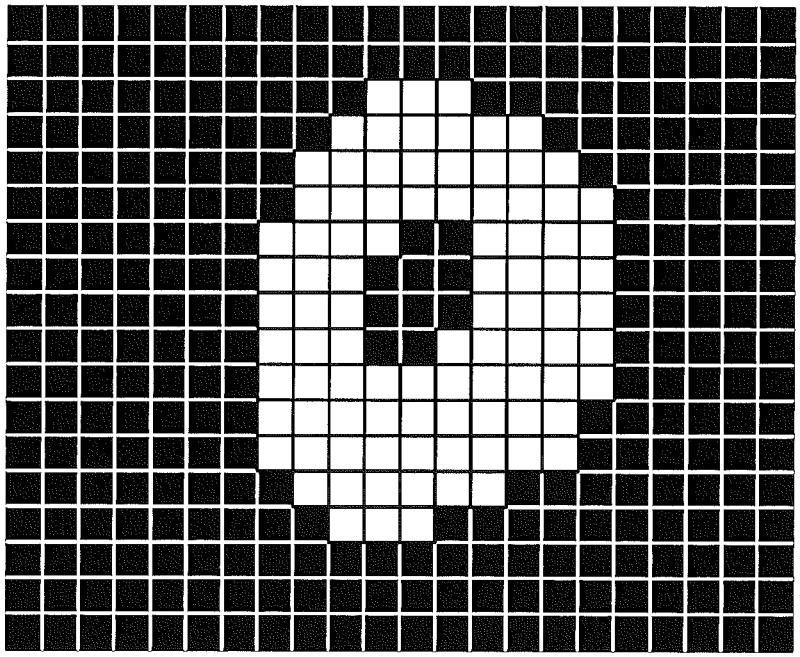
FIG. 15 is a diagram illustrating an example of a result obtained by applying a binarization process and an erosion/dilation process to an image of a differentiated colony whose center part is differentiated.

Here, an example of a result obtained by applying the binarization process and erosion/dilation process (Step #405 and Step #406 in FIG. 9) to an image of the undifferentiated colony shown in FIG. 12 is given in FIG. 14. In FIG. 14, a mass of white pixels is in an elliptic shape. Whereas, an example of a result obtained by applying the binarization process and erosion/dilation process to an image of the differentiated colony 1 shown in FIG. 13 is given in FIG. 15. In FIG. 15, the mass of white pixels in an elliptic shape contains a mass of black pixels in an elliptic shape smaller than that.

Figure 16:
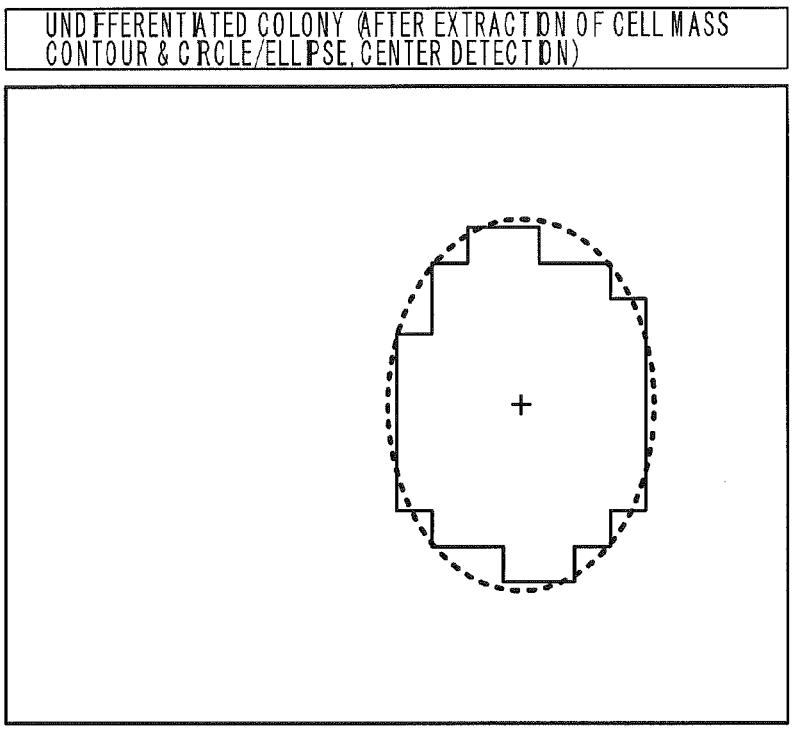
FIG. 16 is a diagram illustrating an example of a result obtained by further applying contour extraction, circle/ellipse detection, and circle/ellipse center detection to an image of an undifferentiated colony.
Figure 17:
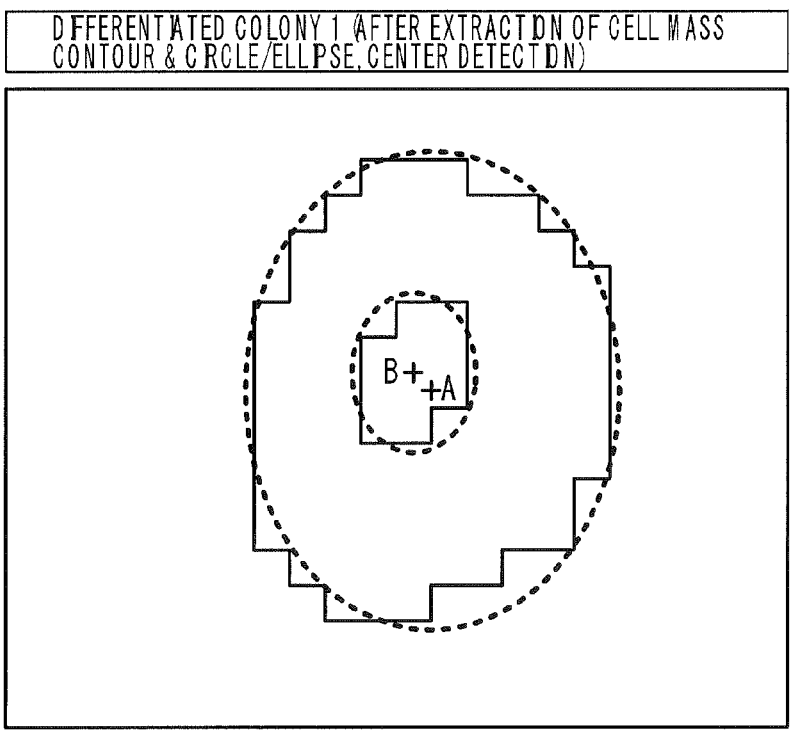
FIG. 17 is a diagram illustrating an example of a result obtained by further applying contour extraction, circle/ellipse detection, and circle/ellipse center detection to an image of an undifferentiated colony.

Further, examples of results obtained by performing contour extraction at Step #512 for these masses of white pixels are indicated by solid lines in FIGS. 16 and 17, respectively. Furthermore, examples of results obtained by performing circle/ellipse detection at Step #513 for the figures of these contours are indicated by broken lines in FIGS. 16 and 17, respectively. Then, examples of results obtained by performing circle/ellipse center detection at Step #514 for these ellipses are indicated by a symbol "+" in FIGS. 16 and 17, respectively.

As the result of circle/ellipse detection at Step #513, only one circle or ellipse is detected in the undifferentiated colony as illustrated in FIG. 16. Whereas, in the differentiated colony 1, two circles or ellipses are detected as illustrated in FIG. 17, and they are formed in a so-called doughnut shape in which one contains the other. The so-called doughnut shape may include a case where one circle or ellipse is inscribed in the other circle or ellipse.

Subsequently, the observation program 220 is executed to determine a state of the cell mass on the basis of the shape information of the circle or ellipse extracted at Step #512 to Step #514 (Step #515 and Step #516).

Specifically, if a plurality of circles or ellipses are detected and a distance between the centers of two of them is equal to or smaller than a predetermined distance (Yes at Step #515), it is determined to be a differentiated colony (predetermined state). Even in an undifferentiated colony, double contour lines might be extracted, and a plurality of circles or ellipses having the centers substantially at the same location might be detected. Thus, in an embodiment of the present invention, if a distance between the centers of two circles or ellipses is equal to or smaller than a predetermined distance (Yes at Step #515), as well as a difference in radii of them is equal to or greater than the predetermined value (Yes at Step #516), it is determined to be a differentiated colony.

Here, assuming that the threshold value Td of a distance between the centers of two circles or ellipses and the threshold value Tr of a radius difference therebetween are equal, if (distance between the centers)≤Td=Tr≤(radius difference), that is, in the case of a so-called doughnut shape in which two circles or ellipses are in such a relationship that one is contained in the other or one is inscribed in the other, it is determined to be a differentiated colony. By setting Td smaller than Tr, the criteria for detecting the so-called doughnut shape can be made strict so that it is determined to be a differentiated colony only if one of the two circles or ellipses contains the other. To the contrary, considering that an image picked up in the entire image-pickup process is used, by setting Td slightly greater than Tr so as to relax the criteria for detecting the so-called doughnut shape, it can be determined to be a differentiated colony including a case where two circles or ellipses are slightly crossed with each other.

Whereas, if only one circle or ellipse is detected (No at Step #515), if distances between the centers are all greater than the predetermined distance (No at Step #515), or if the radius differences are all smaller than the predetermined value (No at Step #516), it is determined to be an undifferentiated colony.

Then, if it is determined to be an undifferentiated colony, the observation program 220 is executed to select the mass of white pixels (cell mass) as a magnifying observation target cell mass, and the subsequent operation flows are the same as Step #412 to Step #415, Step #419, and Step #421 in a third embodiment of the present invention (Step #517 to Step #522). Whereas, if it is determined to be a differentiated colony, it is not selected as the magnifying observation target cell mass, but the subsequent white pixel mass (cell mass) is selected as a target to be determined on whether it is the magnifying observation target cell mass (Step #522), the operation returns to Step #511, and it is determined whether the selected cell mass is of a size equal to or greater than a predetermined size.

As such, since the differentiated colony is detected as the predetermined shape (so-called doughnut shape), the undifferentiated colony can be automatically selected as a cell mass having an appropriate shape for continuing the observation. As a result, the magnifying observation is not conducted for differentiated colonies, and observation of an undifferentiated colony can proceed more efficiently.

In a differentiated colony illustrated in FIG. 18 (hereinafter referred to as a differentiated colony 2), for example, a differentiated region is generated in a peripheral part of the colony, and if the binarization process is executed, the colony results in a mass of white pixels constituted by only undifferentiated regions at the center part. In order to prevent the differentiated colony 2 from being selected as a target of the magnified observation, it is only necessary to execute a ternarization process or a conversion process into four-values instead of the binarization process, for example.

Figure 18:
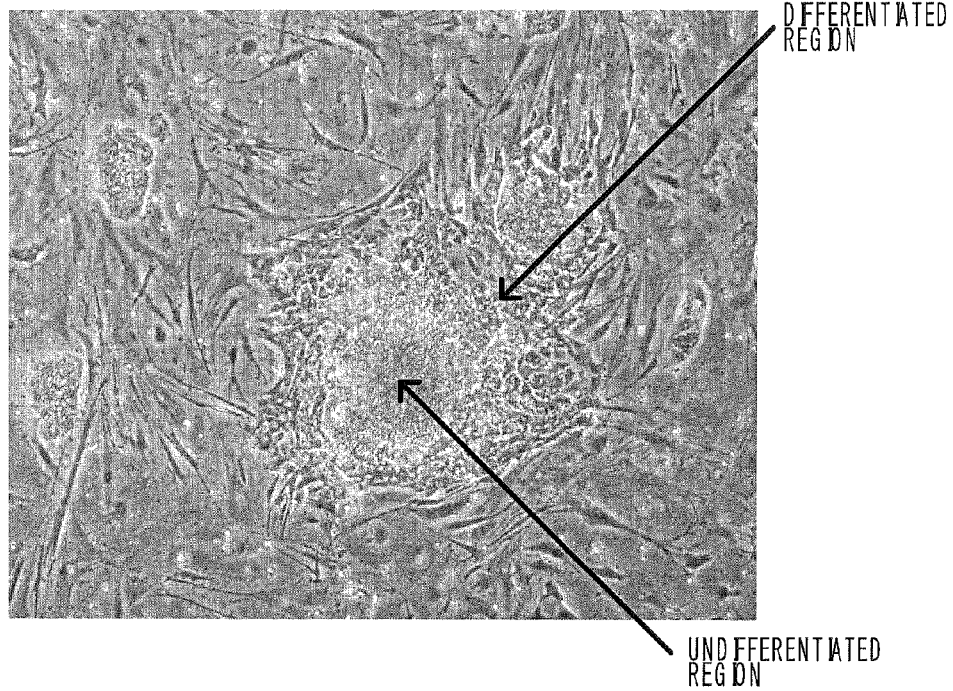
FIG. 18 is a diagram illustrating a differentiated colony whose peripheral part is differentiated as an example of a cell mass having a shape not appropriate for continuing observation.
Figure 19:
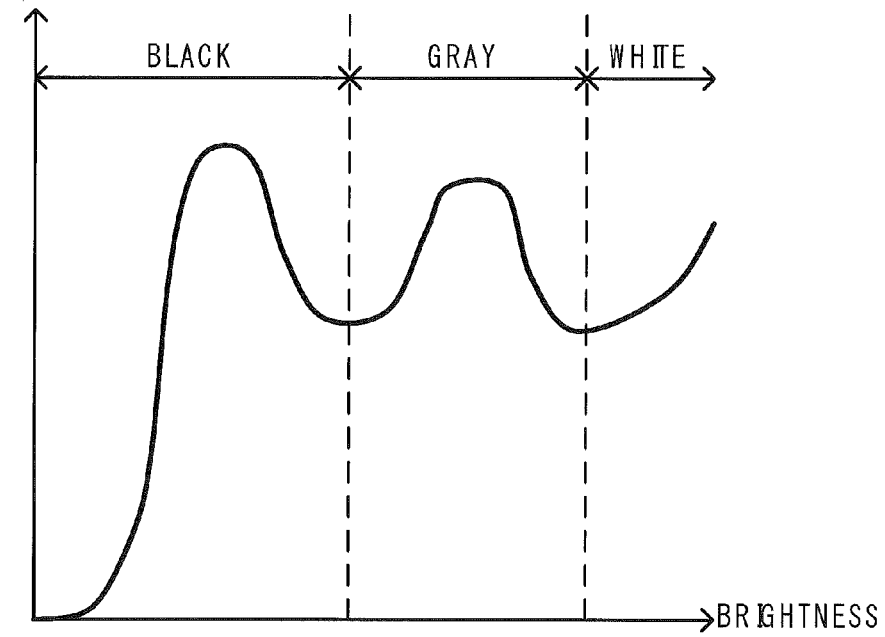
FIG. 19 is a histogram illustrating an example of frequency distribution of brightness of each pixel in an image of a differentiated colony whose peripheral part is differentiated.
Figure 20:
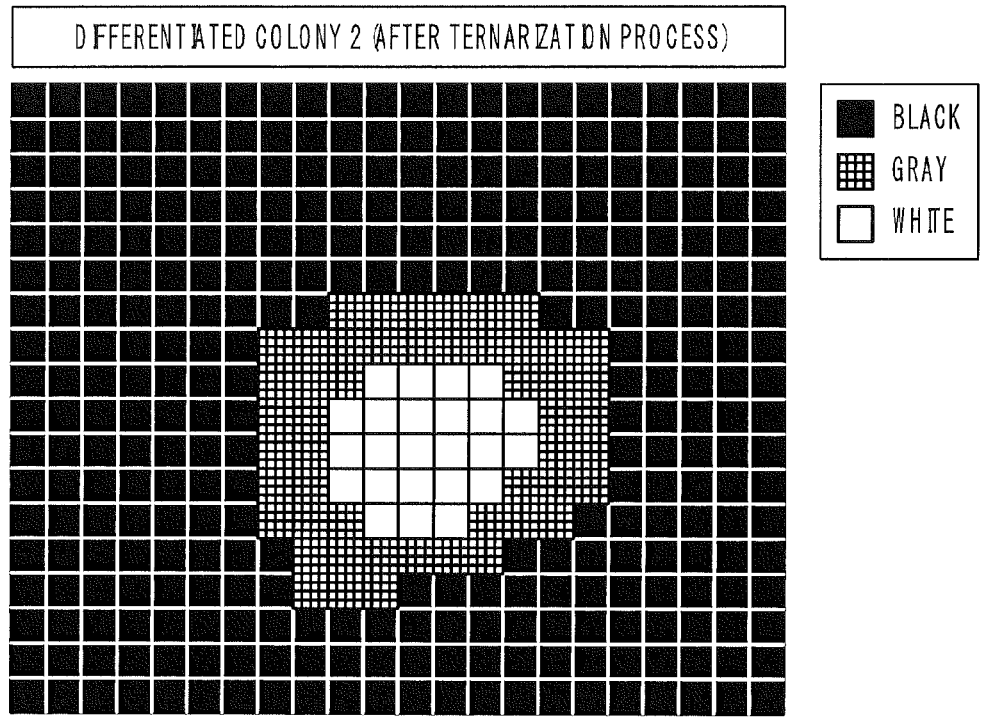
FIG. 20 is a diagram illustrating an example of a result obtained by applying a ternarization process to an image of a differentiated colony whose peripheral part is differentiated.
Figure 21:
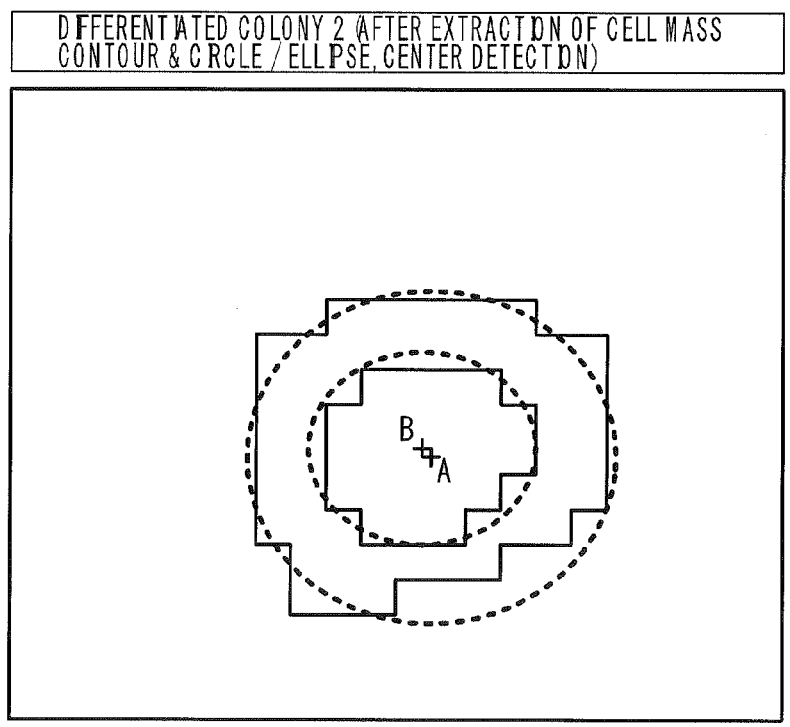
FIG. 21 is a diagram illustrating an example of a result obtained by further applying contour extraction, circle/ellipse detection, and circle/ellipse center detection to an image of a differentiated colony whose peripheral part is differentiated.

FIG. 20 illustrates, as an example, a result obtained by acquiring brightness distribution of each pixel as illustrated in FIG. 19 and applying the ternarization process to an image of the differentiated colony 2 illustrated in FIG. 18. Further, FIG. 21 illustrates an example of a result obtained by executing the contour extraction for each of the masses of white pixels and gray pixels at Step #512, and further executing circle/ellipse detection at Step #513 and circle/ellipse center detection at Step #514. The observation program 220 can be executed to determine the state of the cell mass on the basis of the shape information of the circle or ellipse extracted as such (Step #515 and Step #516).

Figure 22:
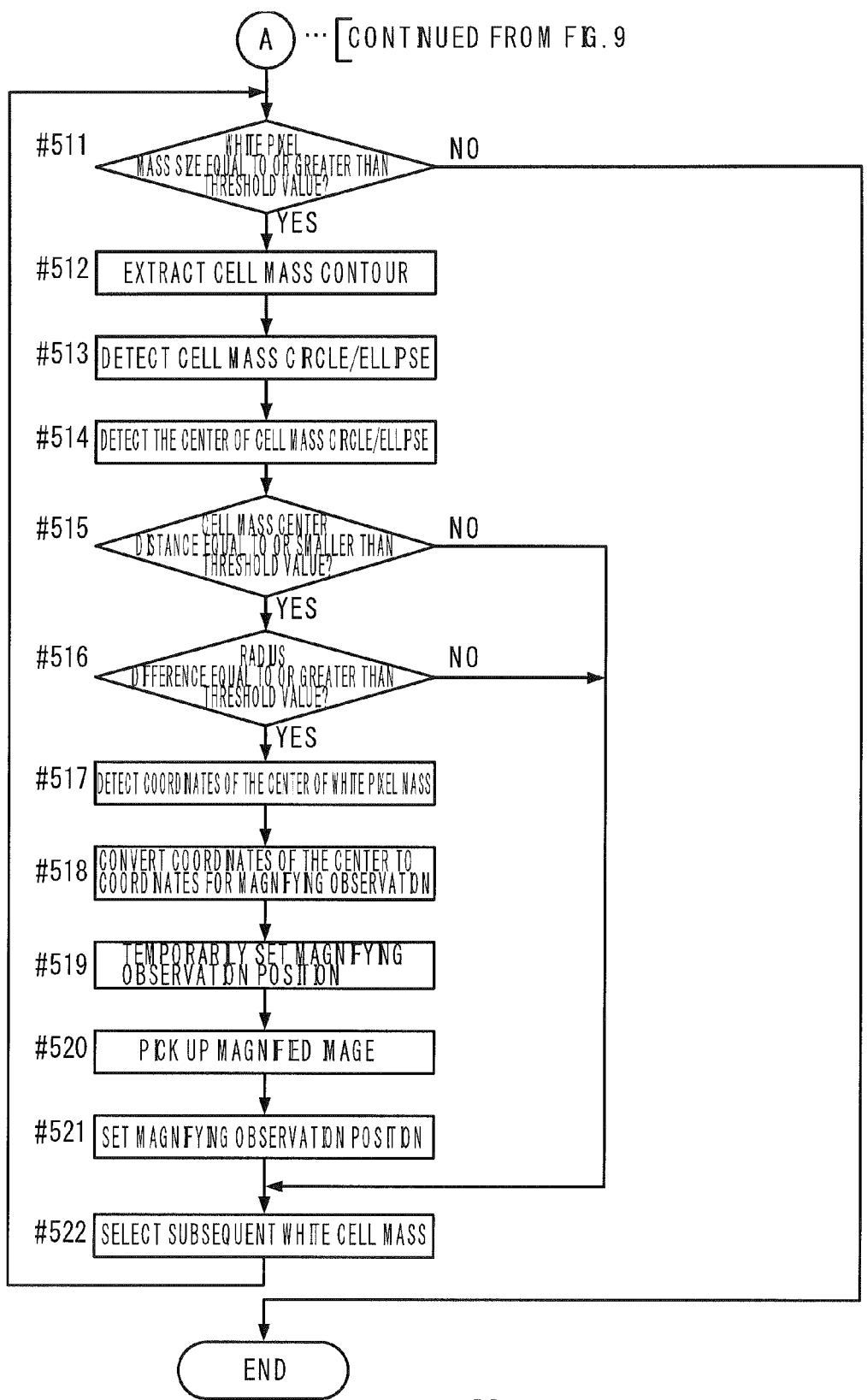
FIG. 22 is a flowchart illustrating an operation according to an observation process in an observation program targeting to a differentiated colony in magnifying observation.

In an embodiment of the present invention, the differentiated colony is set in a predetermined state where the magnifying observation is not conducted, but as illustrated in FIG. 22, the predetermined state (Yes at Step #515 and Yes at Step #516) may be used as a magnifying observation target. In this case, the magnifying observation is not conducted for the undifferentiated colony but only the differentiated colony (predetermined state) can be observed efficiently.

As described above, in the observation program according to a fourth embodiment of the present invention, the shape information of the cell mass identified from the image picked up in the entire image-pickup process at Step #403 is extracted, and the state of the cell mass is determined on the basis of the shape information so that the undifferentiated colony can be automatically selected as a cell mass having an appropriate shape for continuing observation, thereby being able to lower the observation priority of the differentiated colony and stop the observation. The differentiated colony can be also selected as a cell mass having an appropriate shape for continuing observation.

Further, by selecting a magnifying observation target cell mass on the basis of the determination result of the state of the cell mass obtained based on the shape information, the observation of the undifferentiated colony can proceed more efficiently without conducting the magnifying observation for the differentiated colony. The differentiated colony may be used as a magnifying observation target.

Further, in the case where a circle or ellipse is detected from the figure of a contour of a cell mass and a plurality of the circles or ellipses are detected, if a distance between the centers of two of them is equal to or smaller than a predetermined distance, the colony is determined to be a differentiated colony, thereby being able to detect the differentiated colony as a so-called doughnut shape.

Further, if the distance between the centers of the two circles or ellipses is equal to or smaller than a predetermined distance as well as a difference in radii thereof is equal to or greater than the predetermined value, the colony is determined to be a differentiated colony, thereby being able to detect the differentiated colony as a so-called doughnut shape with higher accuracy.

Further, a magnifying observation target cell mass is selected from cell masses each having a size equal to or greater than a predetermined size, thereby being able to determine a time of emergence of a cell mass, and conduct observation continuously from a time of emergence of the cell mass to a time of completion of growth thereof.

The observation process is executed in every predetermined image-pickup period, and when the predetermined observation deadline is reached, the observation process is finished, thereby being able to conduct the time-lapse observation continuously from a time of emergence of the cell mass to a time of completion of growth thereof.

Further, as described above, by picking up an image of the cell in the container C such that an image of the entire container C is picked up using the CMOS camera 12 that is an image-pickup unit of the entire observation unit 10, the observation program causes the computer to extract shape information of the cell mass that has been identified from an image picked up in the entire image-pickup process, and based on the shape information, the state of the cell mass can be determined.

Further, the magnifying observation target cell mass is selected on the basis of the determination result of the state of the cell mass obtained based on the shape information, thereby being able to magnify a part of the region in the container C and pick up an image of the magnifying observation target cell mass by the CCD camera 24 that is an image-pickup unit of the magnifying observation unit 20.

For example, in embodiments described above, a description has been given assuming that a single culture container is to be observed, but a plurality of containers may be observed concurrently by using a tray on which a plurality of culture containers can be placed.

Further, in embodiments described above, the CMOS camera 12 is used for the image pickup unit of the entire observation unit 10 and the CCD camera 24 is used for the image pickup unit of the magnifying observation unit 20, but a type of the camera to be used may be either the CMOS camera or the CCD camera.

Further, in a fourth embodiment of the present invention, by employing Step #416 to Step #420 in a third embodiment of the present invention instead of Step #518, the shape determination in third and fourth embodiments of the present invention may be used in combination.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. A non-transitory recording medium having an observation program recorded therein, the observation program configured to cause a computer to execute:
    an entire image-pickup process of picking up an image of a sample by picking up an image of an entire container containing the sample and a solution;
    a sample mass identification process of identifying a sample mass having a plurality of the samples gathering therein, from the image picked up in the entire image-pickup process;
    a sample mass determination process of extracting shape information of the sample mass identified in the sample mass identification process, and determining a state of the sample mass based on the shape information;
    a coordinate detection process of selecting a magnifying observation target sample mass from the sample masses identified in the sample mass identification process, and detecting coordinates of a center of the magnifying observation target sample mass, based on a determination result of the sample mass determination process; and
    a magnifying image-pickup process of performing magnification with the coordinates detected in the coordinate detection process as a center of the magnification, and picking up an image of the magnifying observation target sample mass.

2. The non-transitory recording medium according to claim 1, wherein
    the sample mass determination process includes:
    extracting a contour of the sample mass identified in the sample mass identification process, and detecting a circle or an ellipse from a figure of the extracted contour;
    determining that the sample mass is in a predetermined state, when a plurality of the circles or the ellipses are detected and a distance between centers of two of the circles or the ellipses is equal to or smaller than a predetermined distance; and
    not selecting the sample mass determined to be in the predetermined state in the sample mass determination process, as the magnifying observation target sample mass.

3. The non-transitory recording medium according to claim 1, wherein
    the sample mass determination process includes:
    extracting a contour of the sample mass identified in the sample mass identification process, and detecting a circle or an ellipse from a figure of the extracted contour;
    determining that the sample mass is in a predetermined state, when a plurality of the circles or the ellipses are detected and a distance between centers of two of the circles or the ellipses is equal to or smaller than a predetermined distance; and
    selecting the sample mass determined to be in the predetermined state in the sample mass determination process, as the magnifying observation target sample mass.

4. The non-transitory recording medium according to claim 2, wherein
    the sample mass determination process includes determining that the sample mass is in the predetermined state, when a plurality of the circles or the ellipses are detected and a distance between centers of two of the circles or the ellipses is equal to or smaller than a predetermined distance and a difference in radii of the two of the circles or the ellipses is equal to or greater than a predetermined value.

5. The non-transitory recording medium according to claim 3, wherein
the sample mass determination process includes determining that the sample mass is in the predetermined state, when a plurality of the circles or the ellipses are detected and a distance between centers of two of the circles or the ellipses is equal to or smaller than a predetermined distance and a difference in radii of the two of the circles or the ellipses is equal to or greater than a predetermined value.

6. The non-transitory recording medium according to claim 1, wherein
the coordinate detection process includes selecting the magnifying observation target sample mass from the sample masses each having a size equal to or greater than a predetermined size, among the sample masses identified in the sample mass identification process, based on a determination result of the sample mass determination process.

7. The non-transitory recording medium according to claim 6, wherein
a time-measuring process of measuring time periods and days from start of observation of the sample is further executed; and
the sample mass identification process includes repeating identification of the sample mass in every predetermined time period relating to identification of the sample mass measured in the time-measuring process, and stopping the identification of the sample mass on condition that the predetermined number of days have elapsed.

8. An observation apparatus comprising:
a computer configured to execute an observation program recorded in the non-transitory recording medium according to claim 1;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

9. An observation apparatus comprising:
a computer configured to execute an observation program recorded in the non-transitory recording medium according to claim 2;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

10. An observation apparatus comprising:
a computer configured to execute an observation program recorded in the non-transitory recording medium according to claim 3;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

11. An observation apparatus comprising:
a computer configured to execute an observation program recorded in the non-transitory recording medium according to claim 4;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

12. An observation apparatus comprising:
a computer configured to execute an observation program recorded in the non-transitory recording medium according to claim 5;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

13. An observation apparatus comprising:
a computer configured to execute an observation program recorded in the non-transitory recording medium according to claim 6;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

14. An observation apparatus comprising:
a computer configured to execute an observation program recorded in the non-transitory recording medium according to claim 7;
a first image pickup unit configured to pick up an image of the sample in the container by picking up an image of the entire container; and
a second image pickup unit configured to perform magnification with the coordinates detected in the coordinate detection process as a center of the magnification, and pick up an image of the sample in the container.

* * * * *